(12) United States Patent
Marks et al.

(10) Patent No.: US 8,609,902 B2
(45) Date of Patent: Dec. 17, 2013

(54) ORGANOACTINIDE-, ORGANOLANTHANIDE-, AND ORGANOGROUP-4-MEDIATED HYDROTHIOLATION OF TERMINAL ALKYNES WITH ALIPHATIC, AROMATIC AND BENZYLIC THIOLS

(75) Inventors: Tobin J. Marks, Evanson, IL (US); Charles J. Weiss, Richland, WA (US); Stephen D. Wobser, Evanston, IL (US)

(73) Assignee: Northwestern University, Evanston, IL (US)

( * ) Notice: Subject to any disclaimer, the term of this patent is extended or adjusted under 35 U.S.C. 154(b) by 382 days.

(21) Appl. No.: 12/856,154

(22) Filed: Aug. 13, 2010

(65) Prior Publication Data
US 2011/0040098 A1   Feb. 17, 2011

Related U.S. Application Data

(60) Provisional application No. 61/233,541, filed on Aug. 13, 2009.

(51) Int. Cl.
*C07C 381/00*   (2006.01)
(52) U.S. Cl.
USPC .................. 568/69; 568/18; 568/38; 568/58; 568/59; 568/61
(58) Field of Classification Search
None
See application file for complete search history.

(56) References Cited

PUBLICATIONS

Kuniyasu, H. et al. "The first example of transition-metal catalyzed addition of aromatic thiols to acetylenes," JACS (1992) 114: 5902-5903.*
Ackermann, L. et al., "Use of Group 4 Bis(sulfonamido) Complexes in the Intramolecular Hydroamination of Alkynes and Allenes", J. Am. Chem. Soc. 2003, 125, 11956-11963.
Alonso, F. et al., "Transition-Metal-Catalyzed Addition of Heteroatom-Hydrogen Bonds to Alkynes", Chem. Rev. 2004, 104, 3079-3160.
Ananikov, V. P. et al., "Nickel (II) Chloride-Catalyzed Regioselective Hydrothiolation of Alkynes", Adv. Synth. Catal. 2005, 347, 1993-2001.
Ananikov, V. P. et al., "New Approach for Size- and Shape-Controlled Preparation of Pd Nanoparticles with Organic Ligands. Synthesis and Application in Catalysis", J. Am. Chem. Soc. 2007, 129, 7252-7253.
Ananikov, V. P. et al., "Efficient and Convenient Synthesis of β-Vinyl Sulfides in Nickel-Catalyzed Regioselective Addition of Thiols to Terminal Alkynes under Solvent-Free Conditions", Organometallics 2006, 25, 1970-1977.
Ananikov, V. P. et al., "Nickel-catalyzed addition of benzenethiol to alkynes: formation of carbon-sulfer and carbon-carbon bonds", Russ. Chem. Bull. 2006, 55, 2109-2113.

Ananikov, Valentine P. et al., "Two Distinct Mechanisms of Alkyne Insertion into the Metal-Sulfur Bond: Combined Experimental and Theoretical Study and Application in Catalysis", Chem. Eur. J. 2010, 16, 2063-2071.
Andrea, T. et al., "Recent advances in organothorium and organouranium catalysis", Chem. Soc. Rev. 2008, 37, 550-567.
Arredondo, V. M. et al., "Organolanthanide-Catalyzed Intramolecular Hydroamination/Cyclization of Aminoallenes", J. Am. Chem. Soc. 1998, 120, 4871-4872.
Arredondo, V. M. et al., "Organolanthanide-Catalyzed Hydroamination/Cyclization. Efficient Allene-based Transformations for the Syntheses of Naturally Occurring Alkaloids", J. Am. Chem. Soc. 1999, 121, 3633-3639.
Arredondo, V. M. et al., "Intramolecular Hydroamination/Cyclization of Aminoallenes Catalyzed by Organolanthanide Complexes. Scope and Mechanistic Aspects", Organometallics 1999, 18, 1949-1960.
Beletskaya, I. P. et al., "Unusual Influence of the Structures of Transition Metal Complexes on Catalytic C-S and C-Se Bond Formation Under Homogeneous and Heterogeneous Conditions", Eur. J. Org. Chem. 2007, 3431-3444.
Beletskaya, I. P. et al., "Addition reactions of E-E and E-H bonds to triple bond of alkynes catalyzed by Pd, Pt, and Ni complexes (E=S, Se)", Pure Appl. Chem. 2007, 79, 1041-1056.
Benati, L. et al., "Free-Radical Reactions of Benzenethiol and Diphenyl Disulphide with Alkynes. Chemical Reactivity of Intermediate 2-(Phenylthio)vinyl Radicals", J. Chem. Soc., Perkin Trans. 1991, 2103-2109.
Benati, L. et al., "A useful method for configurational assignment of vinyl sulfides; stereochemical reassessment of the radical addition of benzenethiol to alkynes", J. Chem. Soc., Perkin Trans. 1995, 1035-1038.
Cao, C. et al., "Rhodium-Catalyzed Alkyne Hydrothiolation with Aromatic and Aliphatic Thiols", J. Am. Chem. Soc. 2005, 127, 17614-17615.
Capella, L. et al., "Radical Sequential Processes Promoted by 1,5-Radical Translocation Reaction: Formation and [3+2] Anulation of Alkenesulfanyl Radicals", J. Org. Chem. 1996, 61, 6783-6789.
Icinose, Y. et al., "Et3B Induced Radical Addition of Thiols to Acetylenes", Chemistry Letters 1987, 8, 1647-1650.
Corma, A. et al., "Efficient synthesis of vinyl and alkyl sulfides via hydrothiolation of alkynes and electron-deficient olefins using soluble and heterogenized gold complexes catalysts", Appl. Catal., A 2010, 375, 49-54.
Cui, D.-M. et al., "Regio- and Stereoselective Au(I)-Catalyzed Intermolecular Hydroalkoxylation of Aryl Allenes", Synlett 2009, 7, 1103-1106.
Delp, S. A. et al., "Addition of S-H Bonds across Electron-Deficient Olefins Catalyzed by Well-Defined Copper(I) Thiolate Complexes", Inorg. Chem. 2007, 46, 2365-2367.
Douglass, M. R. et al., "Organolanthanide-Catalyzed Intramolecular Hydrophosphination/Cyclization of Phosphinoalkenes and Phosphinoalkynes", J. Am. Chem. Soc. 2000, 122, 1824-1825.
Douglass, M. R. et al., "Intramolecular Hydrophosphination/Cyclization of Phosphinoalkenes and Phosphinoalynes Catalyzed by Organolanthanides: Scope, Selectivity, and Mechanism", J. Am. Chem. Soc. 2001, 123, 10221-10238.

(Continued)

*Primary Examiner* — Sudhakar Katakam
(74) *Attorney, Agent, or Firm* — Reinhart Boerner Van Deuren s.c.

(57) ABSTRACT

An efficient and highly Markovnikov selective organoactinide-, organolanthanide-, and organozirconium-catalyzed addition of aryl, benzyl, and aliphatic thiols to terminal alkynes is described. The corresponding vinyl sulfides are produced with little or no side-products.

22 Claims, 4 Drawing Sheets

(56) References Cited

PUBLICATIONS

Dzudza, A. et al., "Efficient Intramolecular Hydroalkoxylation of Unactivated Alkenols Mediated by Recyclable Lanthanide Triflate Ionic Liquids: Scope and Mechanism", Chem. Eur. J. 2010, 16, 3403-3422.

Dzudza, A. et al., "Efficient Intramolecular Hydroalkoxylation/ Cyclization of Unactivated Alkenols Mediated by Lanthanide Triflate Ionic Liquids", Org. Lett. 2009, 11, 1523-1526.

Field, L. D. et al., "Rhodium(I) and iridium(I) complexes containing bidentate phosphine-imidazolyl donor ligands as catalysts for the hydroamination and hydrothiolation of alkynes", Dalton Trans. 2009, 3599-3614.

Fraser, L. R. et al., "Synthesis, Structure, and Hydrothiolation Activity of Rhodium Pyrazolylborate Complexes", Organometallics 2007, 26, 5602-5611.

Gagne, M. R. et al., "Organolanthanide-Catalyzed Hydroamination. A Kinetic, Mechanistic, and Diastereoselectivity Study of the Cyclizaiton of N-Unprotected Amino Olefins", J. Am. Chem. Soc. 1992, 114, 275-294.

Giardello, M. A. et al., "Chiral Organolanthanides Designed for Asymmetric Catalysis. A Kinetic and Mechanistic Study of Enantioselective Olefin Hydroamination/Cyclization and Hydrogenation by C1-Symmetric Me2Si(Me4C5)(C5H3R*) Ln Complexes where R* = Chiral Auxiliary", J. Am. Chem. Soc. 1994, 116, 10241-10254.

Griesbaum, K., "Problems and Possibilities of the Free-Radical Addition of Thiols to Unsaturated Compounds", Angew. Chem. Int. Ed. Engl. 1970, 9, 273-287.

Harkat, H. et al., "Synthesis of functionalized THF and THP through Au-catalyzed cyclization of acetylenic alcohols", Tetrahedron Lett. 2007, 48, 1439-1442.

Hartwig, J. F., "Carbon-heteroatom bond formation catalysed by organometallic complexes", Nature 2008, 455, 314-322.

Haskel, A. et al., "Organoactinide-Catalyzed Intermolecular Hydroamination of Terminal Alkynes", Organometallics 1996, 15, 3773-3775.

Hong, S. et al., "Organolanthanide-Catalyed Hydroamination", Acc. Chem. Res. 2004, 37, 673-686.

Janini, T. E. et al., "1,1,3,3-Tetramethylguanidine solvated lanthanide aryloxides: pre-catalysts for intramolecular hydroalkoxylation", Dalton Trans. 2009, 10601-10608.

Kawaoka, A. M. et al., "Homoleptic Lanthanide Alkyl and Amide Precatalysts Efficiently Mediate Intramolecular Hydrophosphination/Cyclization. Observations on Scope and Mechanism", Organometallics 2003, 22, 4630-4632.

Kondo, T. et al., "Metal-Catalyzed Carbon-Sulfur Bond Formation", Chem. Rev. 2000, 100, 3205-3220.

Kondoh, A. et al., "Stereoselective Hydrothiolation of Alkynes Catalyzed by Cesium Base: Facile Access to (Z)-1-Alkenyl Sulfides", J. Org. Chem. 2005, 70, 6468-6473.

Kondoh, A. et al., "Palladiium-Catalyzed anti-Hydrothiolation of 1-Alkynylphosphines", Org. Lett. 2007, 9, 1383-1385.

Krebs, B. et al., "Transition-Metal Thiolates: From Molecular Fragments of Sulfidic Solids to Models for Active Centers in Biomolecules", Angew. Chem. Int. Ed. Engl. 1991, 30, 769-788.

Kuniyasu, H. et al., "The First Example of Transition-Metal-Catalyzed Addition of Aromatic Thiols to Acetylenes", J. Am. Chem. Soc. 1992, 114, 5902-5903.

Leitch, D. C. et al., "Broadening the Scope of Group 4 Hydroamination Catalysis Using a Tethered Ureate Ligand", J. Am. Chem. Soc. 2009, 131, 18246-18247.

Majumder, S. et al., "Group-4 Dipyrrolylmethane Complexes in Intramolecular Olefin Hydroamination", Organometallics 2008, 27, 1174-1177.

Malyshev, D. A. et al., "Homogeneous Nickel Catalysts for the Selective Transfer of a Single Arylthio Group in the Catalytic Hydrothiolation of Alkynes", Organometallics 2006, 25, 4462-4470.

Marks, T. et al., "Organoactinide-Mediated Hydrothiolation of Terminal Alkynes with Aliphatic, Aromatic, and Benzylic Thiols", J. Am. Chem. Soc. 2009, 131, 2062-2063.

Motta, A. et al., "Energetics and Mechanism of Organolanthanide-Mediated Aminoalkene Hydroamination/Cyclization. A Density Functional Theory Analysis", Organometallics 2004, 23, 4097-4104.

Motta, A. et al., "Energetics and Mechanism of Organolanthanide-Mediated Phosphinoalkene Hydrophosphination/Cyclization. A Density Functional Theory Analysis", Organometallics 2005, 24, 4995-5003.

Motta, A. et al., "Organolanthanide-Catalyzed Hydroamination/ Cyclization Reactions of Aminoalkynes. Computational Investigation of Mechanism, Lanthanide Identity, and Substituent Effects for a Very Exothermic C-N Bond-Forming Process", Organometallics 2006, 25, 5533-5539.

Motta, A. et al., "Atom-Efficient Carbon-Oxygen Bond Formation Processes. DFT Analysis of the Intramolecular Hydroalkoxylation/ Cyclization of Alkynyl Alcohols Mediated by Lanthanide Catalysts", Organometallics 2010, 29, 2004-2012.

Müller, T. E. et al., "Hydroamination: Direct Addition of Amines to Alkenes and Alkynes", Chem. Rev. 2008, 108, 3795-3892.

Nagata, S. et al., "A highly regioselective hydrophosphination of terminal alkynes with tetraphenyldiphosphine in the presence of palladium catalyst", Tetrahedron Lett. 2007, 48, 6637-6640.

Nishina, N. et al., "Gold-catalyzed hydrofunctionalization of allenes with nitrogen and oxygen nucleophiles and its mechanistic insight", Tetrahedron 2009, 65, 1799-1808.

Nishina, N. et al., "Gold-catalyzed intermolecular hydroalkoxylation of allenes; difference in mechanism between hydroalkoxylation and hydroamination", Tetrahedron Lett. 2008, 49, 4908-4911.

Ogawa, A. et al., "Highly Regio- and Stereocontrolled Synthesis of Vinyl Sulfides via Transition-Metal-Catalyzed Hydrothiolation of Alkynes with Thiols", J. Am. Chem. Soc. 1999, 121, 5108-5114.

Perrier, A. et al., "First Titanium-Catalyzed 1,4-Hydrophosphination of 1,3-Dienes", Chem. Eur. J. 2010, 16, 64-67.

Qian, H. et al., "Platinum-Catalyzed Intramolecular Hydroalkoxylation of γ- and δ-Hydroxy Olefins to Form Cyclic Ethers", J. Am. Chem. Soc. 2004, 126, 9536-9537.

Sabarre, A.; Love, J., "Synthesis of 1,1-Disubstituted Olefins via Catalytic Alkyne Hydrothiolation/Kumada Cross-Coupling", Org. Lett. 2008, 10, 3941-3944.

Sadow, A. D. et al., "Nickel(II)-Catalyzed Highly Enantioselective Hydrophosphination of Methacrylonitrile", J. Am. Chem. Soc. 2004, 126, 14704-14705.

Seo, S. et al., "Lanthanide-Catalyst-Mediated Tandem Double Intramolecular Hydroalkoxylation/Cyclization of Dialkynyl Dialcohols: Scope and Mechanism", Chem.-Eur. J. 2010, 16, 5148-5162.

Seo, S. et al., "Intramolecular Hydroalkoxylation/Cyclization of Alkynyl Alcohols Mediated by Lanthanide Catalysts. Scope and Reaction Mechanism", J. Am. Chem. Soc. 2009, 131, 263-276.

Shoai, S. et al., "Catalytic Alkyne Hydrothiolation with Alkanethiols using Wilkinson's Catalyst", Organometallics 2007, 26, 5778-5781.

Smolensky, E. et al., "Intermolecular Hydroamination of Methylenecyclopropane Catalyzed by Group IV Metal Complexes", Organometallics 2007, 26, 4510-4527.

Stephan, D. W. et al., "Early transition metal thiolates", Coord. Chem. Rev. 1996, 147, 147-208.

Stubbert, B. D. et al., "Mechanistic Investigation of Intramolecular Aminoalkene and Aminoalkyne Hydroamination/Cyclization Catalyzed by Highly Electrophilic, Tetravalent Constrained Geometry 4d and 5f Complexes. Evidence for an M-N σ-Bonded Insertive Pathway", J. Am. Chem. Soc. 2007, 129, 6149-6167.

Stubbert, B. D.; Marks, T. J., "Constrained Geometry Organoactinides and Versatile Catalysts for the Intramolecular Hydroamination/Cyclization of Primary and Secondary Amines Having Diverse Tethered C-C Unsaturation", J. Am. Chem. Soc. 2007, 129, 4253-4271.

Stubbert, B. D.; Stern, C. L.; Marks, T. J., "Synthesis and Catalytic Characteristics of Novel Constrained-Geometry Organoactinide Catalysts. The First Example of Actinide-Mediated Intramolecular Hydroamination", Organometallics 2003, 22, 4836-4838.

(56) References Cited

OTHER PUBLICATIONS

Takaki, K. et al., "Intermolecular Hydrophosphination of Alkynes and Related Carbon-Carbon Multiple Bonds Catalyzed by Organoytterbiums", J. Org. Chem. 2003, 68, 6554-6565.

Wicht, D. K. et al., "Platinum-Catalyzed Acrolonitrile Hydrophosphination via Olefin Insertion into a Pt-P Bond", J. Am. Chem. Soc. 1997, 119, 5039-5040.

Yang, C. G. et al., "Intramolecular Additions of Alcohols and Carboxylic Acids to Inert Olefins Catalyzed by Silver(I) Triflate", Org. Lett. 2005, 7, 4553-4556.

Yu, X. et al., "Effective, Selective Hydroalkoxylation/Cyclization of Alkynyl and Allenyl Alcohols Mediated by Lanthanide Catalysts", J. Am. Chem. Soc. 2007, 129, 7244-7245.

Zhang, Z. et al., "Highly Active Au(I) Catalyst for the Intramolecular exo-Hydrofunctionalization of Allenes with Carbon, Nitrogen, and Oxygen Nucleophiles", J. Am. Chem. Soc. 2006, 128, 9066-9073.

Zhang, Z. et al., "Regio- and Stereoselective Synthesis of Alkyl Allylic Ethers via Gold(I)-Catalyzed Intermolecular Hydroalkoxylation of Allenes with Alcohols", Org. Lett. 2008, 10, 2079-2081.

* cited by examiner

[Cp*₂SmCH(TMS)₂],

[1-Hexyne] (M)

ORGANOACTINIDE-, ORGANOLANTHANIDE-, AND ORGANOGROUP-4-MEDIATED HYDROTHIOLATION OF TERMINAL ALKYNES WITH ALIPHATIC, AROMATIC AND BENZYLIC THIOLS

This application claims priority benefit from application Ser. No. 61/233,541 filed Aug. 13, 2009—the entirety of which is incorporated herein by reference.

This invention was made with government support under Grant No. CHE-0809589 awarded by the National Science Foundation. The government has certain rights in the invention.

FIELD OF THE INVENTION

The present invention relates generally to atom-efficient organoactinide-, organolanthanide-, and organoGroup-4-catalyzed intermolecular hydrothiolation of terminal alkynes or allenes. The methods of the invention can be used to incorporate sulfur into organic frameworks, to synthesize carbon-carbon bond forming reagents, and to synthesize vinyl cross-coupling reagents.

BACKGROUND OF THE INVENTION

Sulfur is a constituent of many important polymeric materials, natural products, and synthetic reagents, providing impetus to devise efficient catalytic methodologies for sulfur-carbon bond formation. The addition of S—H bonds across alkynes is an atom-economical route to a variety of vinyl sulfides that can be achieved by several pathways, including radical (Capella, L. et al., *J. Org. Chem.* 1996, 61, 6783-6789; Benati, L. et al., *J. Chem. Soc., Perkin Trans.* 1995, 1035-1038; Benati, L. et al., *J. Chem. Soc., Perkin Trans.* 1991, 2103-2109; Ichinose, Y. et al., *Chem. Lett.* 1987, 16, 1647-1650; Griesbaum, K., *Angew. Chem. Int. Ed. Engl.* 1970, 9, 273-287) and catalytic processes (Sabarre, A.; Love, J., *Org. Lett.* 2008, 10, 3941-3944; Corma, A. et al., *Appl. Catal., A* 2010, 375, 49-54; Ananikov, Valentine P. et al., *Chem. Eur. J.* 2010, 16, 2063-2071; Shoai, S. et al., *Organometallics* 2007, 26, 5778-5781; Kondoh, A. et al., *Org. Lett.* 2007, 9, 1383-1385; Fraser, L. R. et al., *Organometallics* 2007, 26, 5602-5611; Delp, S. A. et al., *Inorg. Chem.* 2007, 46, 2365-2367; Beletskaya, I. P. et al., *Pure Appl. Chem.* 2007, 79, 1041-1056; Beletskaya, I. P. et al., *Eur. J. Org. Chem.* 2007, 3431-3444; Ananikov, V. P. et al., *J. Am. Chem. Soc.* 2007, 129, 7252-7253; Malyshev, D. A. et al., *Organometallics* 2006, 25, 4462-4470; Ananikov, V. P. et al., *Russ. Chem. Bull.* 2006, 55, 2109-2113; Ananikov, V. P. et al., *Organometallics* 2006, 25, 1970-1977; Cao, C. et al., *J. Am. Chem. Soc.* 2005, 127, 17614-17615; Ananikov, V. P. et al., *Adv. Synth. Catal.* 2005, 347, 1993-2001; Kondo, T. et al., *Chem. Rev.* 2000, 100, 3205-3220). Radical hydrothiolation yields unselective mixtures of E and Z vinyl sulfides, while organometallic catalysts offer access to Markovnikov vinyl sulfides or E anti-Markovnikov vinyl sulfides with varying degrees of turnover and selectivity (Misumi, Y. et al., *J. Organomet. Chem.* 2006, 691, 3157-3164). While diverse variants of organometallic complex-mediated hydroelementation have been extensively explored, including hydroamination, hydrophosphination and hydroalkoxylation, only recently has hydrothiolation been investigated in detail due to the historic reputation of sulfur as a catalyst poison (Hegedus, L. L.; McCabe, R. W., *Chemical Industries Series, Vol. 17: Catalyst Poisoning.* 1984), reflecting its high affinity for "soft" transition metal centers (Stephan, D. W. et al., *Coord. Chem. Rev.* 1996, 147, 147-208; Krebs, B. et al., *Angew. Chem. Int. Ed. Engl.* 1991, 30, 769-788).

Interest in homogeneous, catalytic alkyne hydrothiolation over the past few years has yielded a number of metal complexes competent to effect this transformation using late transition metal catalysts (Field, L. D. et al., *Dalton Trans.* 2009, 3599-3614; Ogawa, A. et al., *J. Am. Chem. Soc.* 1999, 121, 5108-5114; Kuniyasu, H. et al., *J. Am. Chem. Soc.* 1992, 114, 5902-5903). For example, Rh, Ir, Ni, Pd, Pt and Au complexes have been previously reported. While some late transition metal catalysts exhibit high activity, achieving high Markovnikov selectivity still presents a challenge, with the exception of Pd, as does competing isomerization of the alkene product, double-thiolation products and product insertion into a second alkyne. Furthermore, while some late transition metal complexes effect efficient alkyne hydrothiolation with benzyl and aryl thiols, few mediate hydrothiolation with the less reactive aliphatic thiols. Previous work with rhodium catalysts demonstrates the ability to utilize both terminal and internal alkynes with selectivity typically favoring the linear E anti-Markovnikov products with the exception of Tp*Rh(PPh$_3$)$_2$, where Markovnikov vinyl sulfides are selectively produced. Studies on group 10 metals find that nickel and palladium catalysts favor the Markovnikov product.

Available mechanistic data for late transition metal-mediated hydrothiolation complexes are consistent with pathways in which the alkyne undergoes insertion into either a metal-hydride or metal-thiolate bond. The accepted hydride pathway for most Rh complexes is initiated by π-coordination/activation of the acetylene to/by the metal-hydride complex, followed by alkyne insertion into the Rh—H bond. Finally, regeneration of the catalyst occurs through reductive elimination of product followed by RS—H oxidative addition to the metal center. Rhodium complexes selectively yield E anti-Markovnikov products as a result of the hydride insertion regiochemistry. In contrast, Pd complexes are proposed to effect hydrothiolation via acetylene insertion into the metal-thiolate bond followed by thiol-mediated displacement of product from the metal center, resulting in Markovnikov selectivity.

The efficacy of inexpensive organozirconium complexes for formally analogous hydroamination processes has been reported (Leitch, D. C. et al., *J. Am. Chem. Soc.* 2009, 131, 18246-18247; Smolensky, E. et al., *Organometallics* 2007, 26, 4510-4527; Ackermann, L. et al., *J. Am. Chem. Soc.* 2003, 125, 11956-11963; Arredondo, V. M. et al., *Organometallics* 1999, 18, 1949-1960; Majumder, S. et al., *Organometallics* 2008, 27, 1174-1177; Stubbert, B. D. et al., *J. Am. Chem. Soc.* 2007, 129, 6149-6167). Likewise, lanthanide complexes have also been used in hydroamination (Andrea, T. et al., *Chem. Soc. Rev.* 2008, 37, 550-567; Miller, T. E. et al., *Chem. Rev.* 2008, 108, 3795-3892; Hartwig, J. F., *Nature* 2008, 455, 314-322; Motta, A. et al., *Organometallics* 2006, 25, 5533-5539; Alonso, F. et al., *Chem. Rev.* 2004, 104, 3079-3160; Motta, A. et al., *Organometallics* 2004, 23, 4097-4104; Hong, S. et al., *Acc. Chem. Res.* 2004, 37, 673-686; Ackermann, L. et al., *J. Am. Chem. Soc.* 2003, 125, 11956-11963; Arredondo, V. M. et al., *Organometallics* 1999, 18, 1949-1960; Arredondo, V. M. et al., *J. Am. Chem. Soc.* 1999, 121, 3633-3639; Arredondo, V. M. et al., *J. Am. Chem. Soc.* 1998, 120, 4871-4872; Haskel, A. et al., Organometallics 1996, 15, 3773-3775; Giardello, M. A. et al., *J. Am. Chem. Soc.* 1994, 116, 10241-10254; Gagne, M. R. et al., *J. Am. Chem. Soc.* 1992, 114, 275-294), hydrophosphination (Perrier, A. et al., *Chem. Eur. J.* 2009, 16, 64-67; Douglass, M. R. et al., *J. Am. Chem. Soc.* 2000, 122, 1824-1825; Douglass, M. R. et al., *J.*

Am. Chem. Soc. 2001, 123, 10221-10238; Kawaoka, A. M. et al., Organometallics 2003, 22, 4630-4632; Motta, A. et al., Organometallics 2005, 24, 4995-5003; Nagata, S. et al., Tetrahedron Lett. 2007, 48, 6637-6640; Sadow, A. D. et al., J. Am. Chem. Soc. 2004, 126, 14704-14705; Takaki, K. et al., J. Org. Chem. 2003, 68, 6554-6565; Wicht, D. K. et al., J. Am. Chem. Soc. 1997, 119, 5039-5040), and hydroalkoxylation processes (Motta, A. et al., Organometallics 2010, 29, 2004-2012; Dzudza, A. et al., Chem.-Eur. J. 2010, 16, 3403-3422; Seo, S. et al., Chem.-Eur. J. 2010, 16, 5148-5162; Cui, D.-M. et al., Synlett 2009, 7, 1103-1106; Dzudza, A. et al., Org. Lett. 2009, 11, 1523-1526; Janini, T. E. et al., Dalton Trans. 2009, 10601-10608; Nishina, N. et al., Tetrahedron 2009, 65, 1799-1808; Seo, S. et al., J. Am. Chem. Soc. 2009, 131, 263-276; Zhang, Z. et al., Org. Lett. 2008, 10, 2079-2081; Nishina, N. et al., Tetrahedron Lett. 2008, 49, 4908-4911; Harkat, H. et al., Tetrahedron Lett. 2007, 48, 1439-1442; Yu, X. et al., J. Am. Chem. Soc. 2007, 129, 7244-7245; Zhang, Z. et al., J. Am. Chem. Soc. 2006, 128, 9066-9073; Yang, C. G. et al., Org. Lett. 2005, 7, 4553-4556; Qian, H. et al., J. Am. Chem. Soc. 2004, 126, 9536-9537). However, the use of these complexes in the hydrothiolation of alkynes has yet to be reported.

Accordingly, an efficient catalytic system is desired for the hydrothiolation of terminal alkynes by aromatic, benzylic, and less reactive aliphatic thiols. This system should proceed with a high degree of Markovnikov selectivity and reduce 1) the formation of double-thiolated side product, 2) the competing isomerization of the alkene product, and 3) the product insertion into a second alkyne.

SUMMARY OF THE INVENTION

In light of the foregoing, it is an object of the present invention to provide an organolanthanide, organoactinide, or organoGroup-4 catalyst for the intermolecular hydrothiolation of terminal alkynes using a variety of aryl, benzyl and aliphatic thiols, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can also be an object of the present invention to provide an efficient method for a catalyzed addition of aryl, benzyl and aliphatic thiols to terminal alkynes to yield vinyl sulfides. In an aspect of the invention, the method is Markovnikov-selective, and the vinyl sulfides produced by the method can also be free, or substantially free, of a double-thiolated side product. Thus, the method comprises treating a thiol with a terminal alkyne in the presence of a catalyst selected from the group consisting of an organolanthanide, organoactinide and organoGroup-4 catalyst to afford a vinyl sulfide.

It is another object of the present invention to provide a vinyl sulfide prepared by treating a thiol with a terminal alkyne in the presence of a catalyst selected from the group consisting of an organolanthanide, organoactinide and organoGroup-4 catalyst.

Other objects, features, benefits and advantages of this invention would be apparent from the summary, in conjunction with the following descriptions of certain embodiments, and will be readily apparent to those skilled in the art. Such objects, features, benefits and advantages will be apparent from the above as to taken into conjunction with the accompanying examples, data, figures and all reasonable inferences to be drawn therefrom, alone or with consideration of the references incorporated herein.

DETAILED DESCRIPTION OF THE INVENTION

Figure 1A:
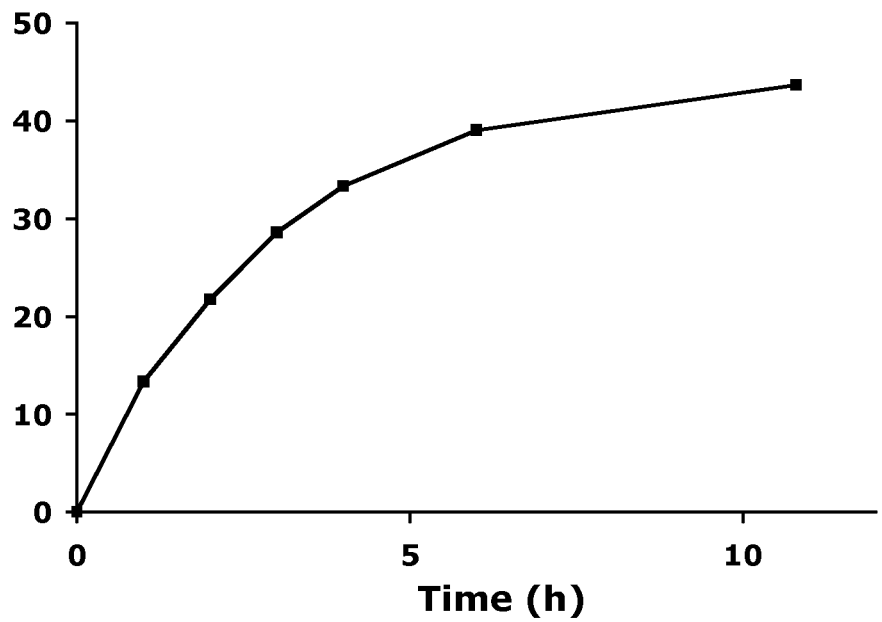
FIG. 1 is a representative plot of product formation rate against time for CGCZrMe$_2$ (Zr-i)-mediated hydrothiolation 1A+2B→3AB. (A) Plot of product formation rate of 1A+2A→3AA versus Zr-i; (B), [2A] and (C) [1A] at (D) [1A] and [2A]=0.2 M.

In part, the present invention can be directed to a method of preparing a vinyl sulfide comprising treating a thiol with a terminal alkyne in the presence of a catalyst selected from the group consisting of CGCM$^1$R$^1{}_2$, wherein M$^1$ is selected from an actinide metal and a Group 4 metal, and R$^1$ is selected from NMe$_2$, NEt$_2$ and Me; CGCM$^2$R$^2$, wherein M$^2$ is lanthanide metal and R$^2$ is N(TMS)$_2$; Cp*$_2$M$^1$R$^3{}_2$, wherein R$^3$ is selected from NMe$_2$, NEt$_2$, Me and CH$_2$TMS; Cp*$_2$M$^2$R$^4$, wherein R$^4$ is selected from N(TMS)$_2$ and CH(TMS)$_2$; Me$_2$SiCp"M$^3$R$^5{}_2$, wherein M$^3$ is an actinide metal, and R$^5$ is selected from CH$_2$TMS and Bn; M[R$^4$]$_3$; Cp*M$^4$R$^6$, wherein M$^4$ is a Group 4 metal and R$^6$ is selected from Bn and Cl$_2$NMe$_2$; and M$^4$(R$^3$)$_4$. In an aspect of the invention, the thiol is selected from aryl, benzyl and aliphatic thiols.

The present invention can also be directed to a method of preparing a vinyl sulfide comprising treating a thiol of the formula I

R"—SH            I with an alkyne of formula II

-R'            II to afford a corresponding vinyl sulfide of formula III

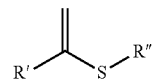

III in the presence of a catalyst selected from the group consisting of CGCM$^1$R$^1{}_2$, wherein M$^1$ is selected from an actinide metal and a Group IV metal, and R$^1$ is selected from NMe$_2$, NEt$_2$ and Me; CGCM$^2$R$^2$, wherein M$^2$ is lanthanide metal and R$^2$ is N(TMS)$_2$; Cp*$_2$M$^1$R$^3{}_2$, wherein R$^3$ is selected from NMe$_2$, NEt$_2$, Me and CH$_2$TMS; Cp*$_2$M$^2$R$^4$, wherein R$^4$ is selected from N(TMS)$_2$ and CH(TMS)$_2$; Me$_2$SiCp"M$^3$R$^5{}_2$, wherein M$^3$ is an actinide metal, and R$^5$ is selected from CH$_2$TMS and Bn; M$^1$[R$^4$]$_3$; Cp*M$^4$R$^6$, wherein M$^4$ is a Group 4 metal and R$^6$ is selected from Bn and Cl$_2$NMe$_2$; and M$^4$(R$^3$)$_4$; and wherein R' and R" are independently selected from the group consisting of alkyl, aryl, heteroaryl, cycloalkyl, arylalkyl, heteroarylalkyl and cycloalkylalkyl.

The general scheme for the hydrothiolation reaction of the invention is depicted in Scheme 1.

Scheme 1

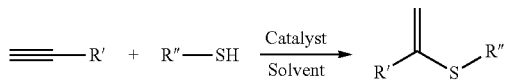

By "alkyl" in the present invention is meant a straight or branched chain alkyl radical having 1-20, and preferably from 1-12, carbon atoms. Examples include but are not limited to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, cycloalkyl, aryl, alkenyl, hydroxy or alkoxy group and the like.

By "aromatic" is meant an "aryl" or "heteroaryl" group.

By "aryl" is meant an aromatic carbocylic radical having a single ring (e.g. phenyl), multiple rings (e.g. biphenyl) or multiple fused rings in which at least one is aromatic (e.g. 1,2,3,4-tetrahydronaphthyl). The aryl group can also be optionally mono-, di-, or trisubstituted with, for example, halo, alkyl, alkenyl, cycloalkyl, hydroxy or alkoxy and the like.

By "heteroaryl" is meant one or multiple fused aromatic ring systems of 5-, 6- or 7-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl. The heteroaryl group can also be optionally mono-, di-, or trisubstituted with, for example, halo, alkyl, alkenyl, cycloalkyl, hydroxy or alkoxy and the like.

By "cycloalkyl" is meant a carbocylic radical having a single ring (e.g. cyclohexyl), multiple rings (e.g. bicyclohexyl) or multiple fused rings (e.g. naphthlene). The cycloalkyl group can optionally contain from 1 to 4 heteroatoms. In addition, the cycloalkyl group may have one or more double bonds. The cycloalkyl group can also be optionally mono-, di-, or trisubstituted with, for example, halo, alkyl, alkenyl, aryl, hydroxy or alkoxy and the like.

By "alkoxy" is meant an oxy-containing radical having an alkyl portion. Examples include, but are not limited to, methoxy, ethoxy, propoxy, butoxy and tert-butoxy. The alkoxy group can also be optionally mono-, di-, or trisubstituted with, for example, halo, aryl, cycloalkyl or hydroxy and the like.

By "alkenyl" is meant a straight or branched hydrocarbon radical having from 2 to 20, and preferably from 2-6, carbon atoms and from one to three double bonds and includes, for example, ethenyl, propenyl, 1-but-3-enyl, 1-pent-3-enyl, 1-hex-5-enyl. The alkenyl group can also be optionally mono-, di-, or trisubstituted with, for example, halo, aryl, cycloalkyl or alkoxy and the like.

By "alkynyl" is meant a straight or branched hydrocarbon radical having from 2 to 20, and preferably from 3-12, carbon atoms and from one to three double bonds and includes, for example, propenyl, 1-but-3-enyl, 1-pent-3-enyl, 1-hex-5-enyl. The alkenyl group can also be optionally mono-, di-, or trisubstituted with, for example, halo, aryl, cycloalkyl or alkoxy and the like.

"Halo" is a halogen radical of fluorine, chlorine, bromine or iodine.

By "Group 4 metal" is meant Ti(IV), Zr(IV) and Hf(IV).

The following abbreviations/structures can be used interchangeably herein:

CGC—$Me_2SiCp''NCMe_3$
Me—Methyl
Et—Ethyl
Bn—Benzyl
TMS—Trimethylsilyl

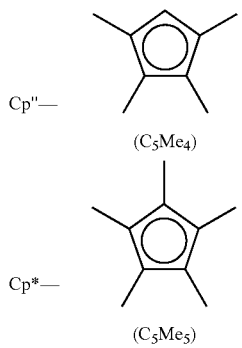

Cp''— ($C_5Me_4$)

Cp*— ($C_5Me_5$)

The present invention can also be directed to a vinyl sulfide of formula III

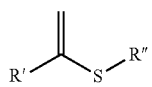

III prepared by the steps comprising the step of reacting a thiol of formula I

R''—SH    I with a terminal alkyne of formula II

≡-R'    II wherein R' and R'' are independently selected from the group consisting of alkyl, aryl, heteroaryl, cycloalkyl, arylalkyl, heteroarylalkyl and cycloalkylalkyl, in the presence of a catalyst selected from the group consisting of $CGCM^1R^1_2$, wherein $M^1$ is selected from an actinide metal and a Group 4 metal, and $R^1$ is selected from $NMe_2$, $NEt_2$ and Me; $CGCM^2R^2$, wherein $M^2$ is lanthanide metal and $R^2$ is $N(TMS)_2$; $Cp^*_2M^1R^3_2$, wherein $R^3$ is selected from $NMe_2$, $NEt_2$, Me and $CH_2TMS$; $Cp^*_2M^2R^4$, wherein $R^4$ is selected from $N(TMS)_2$ and $CH(TMS)_2$; $Me_2SiCp''M^3R^5_2$, wherein $M^3$ is an actinide metal, and $R^5$ is selected from $CH_2TMS$ and Bn; $M[R^4]_3$; $Cp^*M^4R^6$, wherein $M^4$ is a Group 4 metal and $R^6$ is selected from Bn and $Cl_2NMe_2$; and $M^4(R^3)_4$; and isolating the vinyl sulfide.

Preferably, R' is $C_1$-$C_6$-alkyl, aryl, heteroaryl, $C_3$-$C_7$-cycloalkyl, aryl-$C_1$-$C_6$-alkyl, heteroaryl-$C_1$-$C_6$-alkyl or $C_3$-$C_7$-cyloalkyl-$C_1$-$C_6$-alkyl. Non-limiting examples of alkynes include 1-hexyne, ethynylcyclohexane, prop-2-ynylcyclohexane, 1-ethynylcyclohex-1-ene, 3-ethynylpyridine, prop-2-yn-1-amine or ethynylbenzene.

Preferably, R'' is $C_1$-$C_{12}$-alkyl, aryl, heteroaryl, $C_3$-$C_7$-cycloalkyl or aryl-$C_1$-$C_6$-alkyl. Non-limiting examples of thiols include 1-pentanethiol, 1-pentanethiol-d, 1-dodecanethiol, cyclohexanethiol, 2-methyl-2-butanethiol, benzyl mercaptan, 4-methylbenzyl mercaptan, prop-2-yn-1-amine or thiophenol.

Representative examples of suitable catalysts are those depicted in Table 1 below.

TABLE 1

| Lanthanide | Actinide | Group 4 |
|---|---|---|
| 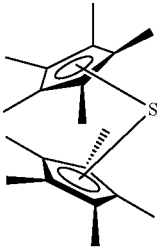<br>Cp*$_2$SmN(TMS)$_2$<br>(Ln-i) | 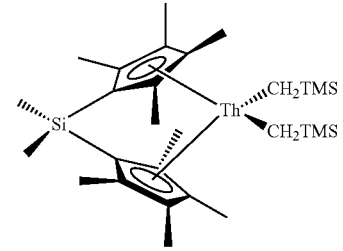<br>Me$_2$SiCp″$_2$Th[CH$_2$(TMS)]$_2$<br>(An-i) | 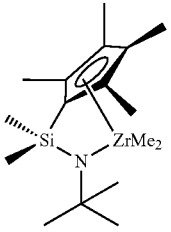<br>CGCZrMe$_2$<br>(Zr-i) |
| 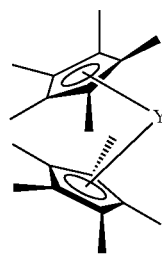<br>Cp*$_2$YCH(TMS)$_2$<br>(Ln-ii) | 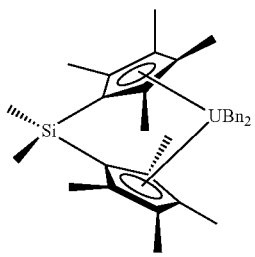<br>Me$_2$SiCp″$_2$UBn$_2$<br>(An-ii) | 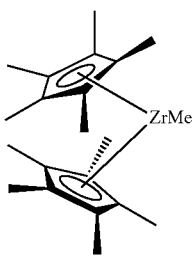<br>Cp*$_2$ZrMe$_2$<br>(Zr-ii) |
| 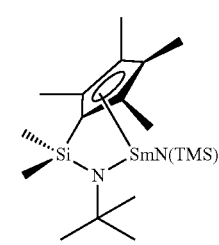<br>CGCSmN(TMS)$_2$<br>(Ln-iii) | 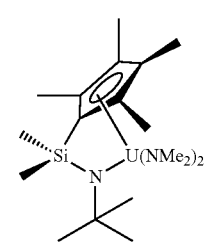<br>CGCU(NMe$_2$)$_2$<br>(An-iii) | 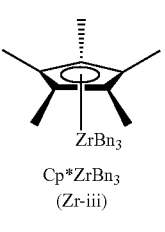<br>Cp*ZrBn$_3$<br>(Zr-iii) |
| La[N(TMS)$_2$]$_3$<br>(Ln-iv) | 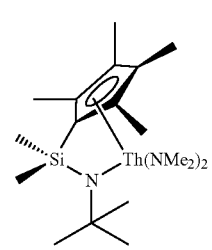<br>CGCTh(NMe$_2$)$_2$<br>(An-iv) | Zr[NMe$_2$]$_4$<br>(Zr-iv) |
| Nd[N(TMS)$_2$]$_3$<br>(Ln-v) | U(NEt$_2$)$_4$<br>(An-v) | Cp*ZrCl$_2$NMe$_2$<br>(Zr-v) |

TABLE 1-continued

| Lanthanide | Actinide | Group 4 |
|---|---|---|
| Lu[CH(TMS)$_2$]$_3$ (Ln-vi) | Cp*$_2$U(NMe$_2$)$_2$ (An-vi) | |
| Y[N(TMS)$_2$]$_3$ (Ln-vii) | Cp*$_2$Th(CH$_2$TMS)$_2$ (An-vii) | |
| Cp*$_2$LaCH(TMS)$_2$ (Ln-viii) | Cp*$_2$U(CH$_2$TMS)$_2$ (An-viii) | |
| Cp*$_2$SmCH(TMS)$_2$ (Ln-ix) | | |
| CP*$_2$LuCH(TMS)$_2$ (Ln-x) | | |

The present hydrothiolation process exhibits a high level of Markovnikov selectivity. This presumably reflects a four-membered transition state, with the alkyne insertion regiochemistry dictated by transition state sterics and bond polarity orientation Marks, T. J. et al., *J. Am. Chem. Soc.* 2009, 131, 2062-2063, incorporated in its entirety herein by reference. Additional competing, non-catalytic, anti-Markovnikov products are occasionally detected under the present reaction conditions. These products are, for the most part, formed in negligible quantities. Anti-Markovnikov side-products can be further suppressed with the addition of a radical inhibitor, as, for example, γ-terpinene, into the reaction mixture. Despite formal similarities to the proposed insertion/protonolysis mechanisms of several Pd and Ni catalysts (Malyshev, D. A. et al., *Organometallics* 2006, 25, 4462-4470), double-thiolated side-products are surprisingly not observed in the instant invention.

Hydrothiolation rates appear to be dependent on the type of thiol used. Changing from primary to secondary aliphatic thiols results in significant rate depression, suggesting steric impediments in the turnover-limiting alkyne insertion. As much as 50× rate reduction is observed in transitioning from a primary to a secondary thiol (Table 2). Aromatic thiol functionality also influences hydrothiolation rates. For example, use of a benzyl mercaptan (1G) or thiophenol increases the turnover frequency (N$_t$) greatly. The enhanced reactivity of aryl- and benzyl-thiols likely reflects electronic factors. However, for benzenethiol, any electronic gain is offset by increased sterics when compared to 1-pentanethiol. The 4-methylbenzyl mercaptan yields the largest thiol substrate N$_t$, likely reflecting a combination of favorable electronics and sterics.

Alkyne structure also affects the rate of hydrothiolation, however steric encumberance exhibits a less pronounced influence than electronic characteristics. Switching from an α-monosubstituted to an α-disubstituted alkyne results in a moderate decrease in rate (Table 2). Similar to the aforementioned trend with thiols, alkyne electronic characteristics also play a prominent role in influencing hydrothiolation rates, with conjugated alkynes exhibiting significantly enhanced rates. In particular, introduction of unsaturation α to the C≡C bond results in a 5× rate increase versus the unconjugated alkyne, while phenylacetylene (2B) increases the activity versus the cyclohexylacetylene (2D). Rate enhancement is also observed with a 3-ethynylpyridine, although not as pronounced as that for phenyl substitution.

TABLE 2

| Thiol | Alkyne | Product | N$_t$ (h$^{-1}$, °C.) |
|---|---|---|---|
| 1A | 2A | 3AA | 5(90) 0.7(120) |

TABLE 2-continued
| Thiol | Alkyne | Product | $N_t$ (h$^{-1}$, °C.) |
|---|---|---|---|
| 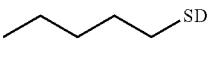 1A-d | 2A | 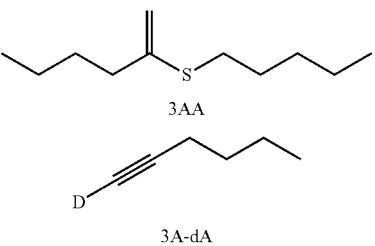 3AA 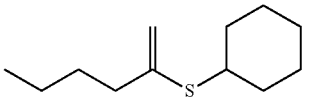 3A-dA | — |
| 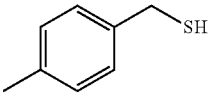 1B | 2A | 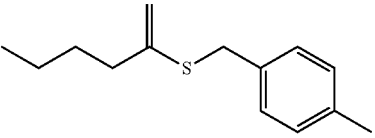 3BA | 1(110) |
| 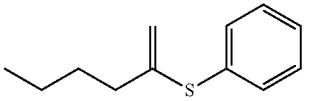 1C | 2A | 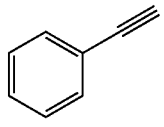 3CA | 14(90) 27(110) |
| 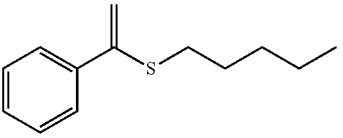 1D | 2A | 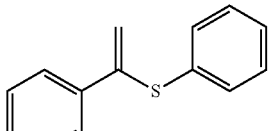 3DA | 4(110) |
| 1A | 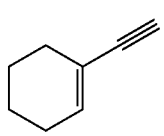 2B | 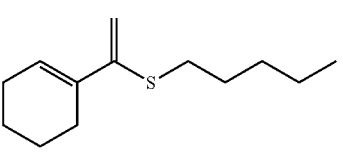 3AB | 5(90) |
| 1D | 2B | 3DB | 8(110) 0.2(120) |
| 1A | 2C | 3AC | 6(110) |

TABLE 2-continued

| Thiol | Alkyne | Product | $N_t$ (h$^{-1}$, °C.) |
|---|---|---|---|
| 1A | 2D | 3AD | 4(110) |
| 1C | 2D | 3CD | 16(90) |
| 1E | 2A | 3EA | 0.6(120) |
| 1F | 2A | 3FA | 0.6(120) |
| 1G | 2A | 3GA | 3(120) |
| 1A | 2E | 3AE | 0.3(120) |
| 1A | 2F | 3AF | 1.5(120) |
| 1A | 2G | 3AG | 1.2(120) |

TABLE 2-continued

| Thiol | Alkyne | Product | $N_t$ (h$^{-1}$, ° C.) |
|---|---|---|---|
| 1A | 2H (HC≡C-CH₂-NH₂) | 3AH (H₂N-CH₂-C(=CH₂)-S-pentyl) | 4.8(120) 4.7(120) |

In spite of some variations in conversion, good to excellent selectivities are observed for all thiols examined with 1-hexyne. Most of the hydrothiolation reactions proceed with >90% Markovnikov selectivity (Table 3). Likewise, selectivity remains high when varying the alkyne, sometimes requiring the presence of a radical inhibitor such as γ-terpinene.

TABLE 3

| Thiol | Alkyne | Catalyst | Selectivity (%) | Conversion (%) |
|---|---|---|---|---|
| 1E | 2A | Ln-ix | >99 | ≥95 |
| 1A | 2A | Ln-ix | >99 | 55 |
| 1B | 2A | Ln-ix | 90 | 11 |
| 1G | 2A | Ln-ix | >99 | 92 |
| 1D | 2A | Ln-ix | 91 | 48 |
| 1E | 2A | Zr-i | 96 | 95 |
| 1A | 2A | Zr-i | 94 | 95 |
| 1B | 2A | Zr-i | 59 | 55 |
| 1G | 2A | Zr-i | 95 | 95 |
| 1D | 2A | Zr-i | 94 | 94 |
| 1A | 2D | Ln-ix | 88 | 26 |
| 1A | 2E | Ln-ix | 95 | 20 |
| 1A | 2F | Ln-ix | 72 | 55 |
| 1A | 2C | Ln-ix | 77 (with γ-terpinene) | 56 |
| 1A | 2B | Ln-ix | 95 (with γ-terpinene) | 39 |
| 1A | 2D | Zr-i | 92 | 92 |
| 1A | 2E | Zr-i | 96 | 98 |
| 1A | 2F | Zr-i | 91 | 100 |
| 1A | 2C | Zr-i | 97 (with γ-terpinene) | 100 |
| 1A | 2B | Zr-i | 66 | 100 |
| 1A | 2D | An-vii | 94 | 32 |
| 1G | 2A | An-vii | 90 | 43 |
| 1D | 2B | An-vii | 83 (with γ-terpinene) | 61 |
| 1A | 2H | Zr-i | 75 | |
| 1A | 2H | Zr-iii | 98 | |

Ancillary ligand selection has consequences for the stability of organolanthanide-, organoactinide- and organozirconium-complexes in hydrothiolation catalysis. While the addition of excess thiol to Ln-iv, for example, results in immediate precipitation, Cp-based ligation delays precipitation. The non-bonded repulsions of the Cp-based ligands likely suppress the formation of insoluble, highly aggregated metal complexes. Also, metal ionic radius exerts an influence on catalyst thiolytic stability, with the smaller ions exhibiting greater resistance to precipitation.

Figure 1B:
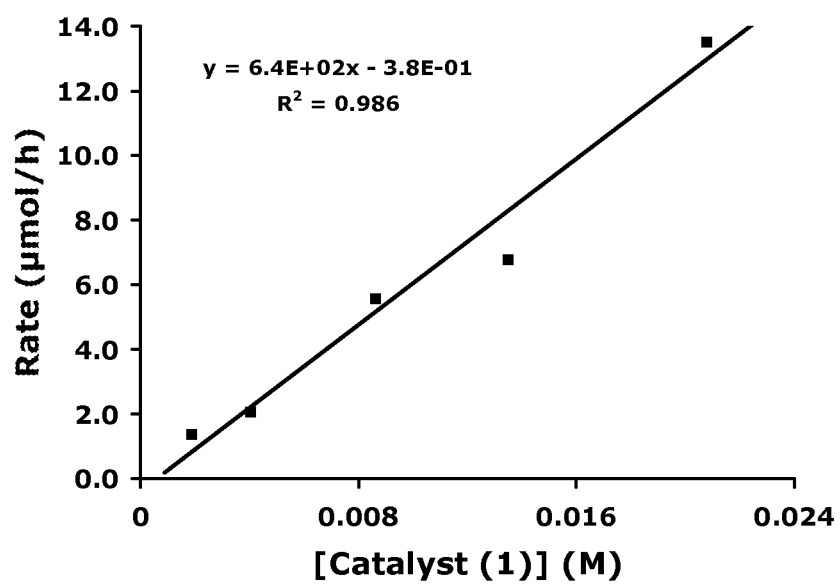
Figure 1C:
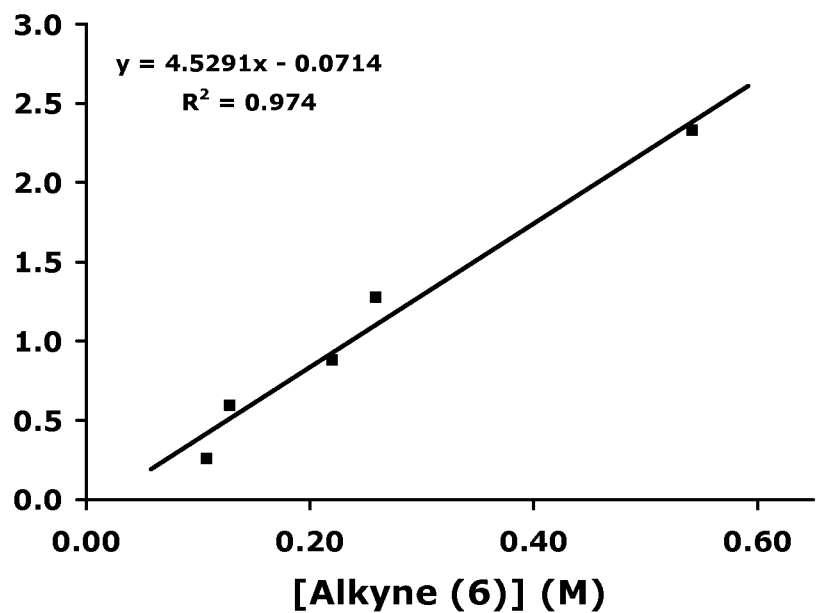
Figure 1D:
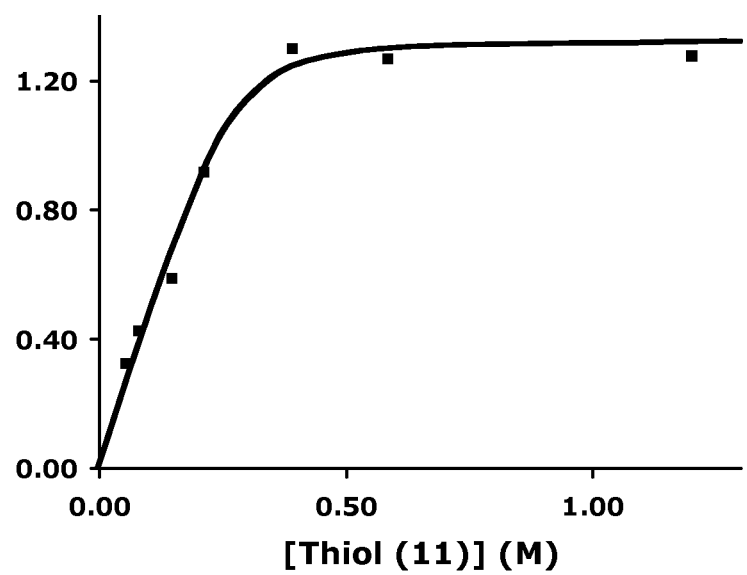

Kinetic studies are performed to define the hydrothiolation reaction pathway and to better understand the influence of [catalyst], [thiol], and [alkyne] on the sequence of reaction events. Experiments are conducted on the CGCZrMe₂ (Zr-i)-mediated hydrothiolation of 1-hexyne (2A) by 1-pentanethiol (1A), and kinetic results are plotted in FIG. 1. The empirical rate law is derived by systematically varying concentration of Zr-i, 1A, and 2A at 120° C. Experiments carried out by varying [Zr-i] over the range 1.9-21 mM exhibit a clear, linear trend when plotted against the measured rate (FIG. 1B) indicating a first-order dependence of rate on catalyst concentration. By varying [2A] over the range 0.10-1.5 M, a first-order trend is also observed in the plot of [2A] versus product formation rate (FIG. 1C). The varying of 1A concentration reveals a more complex trend, with an approximate first-order behavior for [1A]<0.3 M, followed by saturation in the rate at concentrations >0.3 M (FIG. 1D). As a result, the empirical rate law for the reaction 1A+2A→3AA is described by Equation 1a with [Zr-i] and [2A] both first-order, and [1A]x-order with x=1 for [1A]<0.3 M and x=0 for [1A]>0.3 M. Additional catalyst- and alkyne-dependance studies performed under high [thiol] conditions (i.e. [thiol]=1.2 M) show that [alkyne] and [catalyst] remain first-order even at elevated [thiol].

$$\text{Rate} = k_{obs}[\text{Zr-i}]^1[2A]^1[1A]^x \quad \text{(Equation 1a)}$$

To derive activation parameters, the rate of the conversion 1A+2A→3AA mediated by Zr-i is analyzed from 50 to 80° C., and the data are plotted with respect to the Eyring equation. Variable temperature studies at 0.2 M [alkyne] and [thiol] result in an Eyring plot yielding $\Delta H^{\ddagger} = +18.1(1.2)$ kcal/mol and $\Delta S^{\ddagger} = -20.9(2.5)$ e.u. Repeating the temperature studies with [thiol]=1.2 M from 40 to 80° C. yields similar reactions parameters of $\Delta H^{\ddagger} = +17.8(1.5)$ kcal/mol and $\Delta S^{\ddagger} = -24.4(4.8)$ e.u.

To trace the fate of the D—C≡C—R' hydrogens in the present catalytic transformations, deuterium-labeling experiments are performed using deuterated phenylacetylene (2B-d). Upon addition of 1A and 2B-d to Zr-i at room temperature, a single methane (CH₄) resonance is immediately observed in the ¹H NMR spectrum. The absence of CH₃-D suggests exclusive activation of the catalyst by thiol protonolysis despite known alkyne protonolysis activity. To further rule out alkyne-mediated protonolysis as a kinetically signifigant route for the cleavage of Zr-alkyl bonds, relative rates of alkyne- and thiol-mediated protonolysis are examined in the activation of Cp*₂ZrMe₂ (Zr-ii). By addition of either 2A or 1A to Zr-ii, thiol protonolysis of the Zr-Me bonds is measured to be 150× more rapid than the analogous alkyne protonolysis.

An apparent KIE of $k_H/k_D=1.3(0.1)$ is measured for the reaction 1A+2B-d catalyzed by complex Zr-i, consistent with a secondary kinetic isotope effect. At early reaction times, a single olefinic resonance appears in the ¹H NMR at δ 5.13 ppm assigned to a product 3AB-d$_E$ by 1D NOESY NMR. In addition, ²H NMR shows a single product deuterium resonance at δ 5.4 ppm. Upon further heating, additional product olefinic resonances appear in the ¹H NMR spectra at δ 5.41, 5.40, and 5.14 ppm with a second olefinic resonance in the ²H NMR at δ5.1 ppm indicating the formation of products 3AB, 3AB-d$_z$, and possibly 3AB-d₂ (Scheme 2). Interestingly, a deuterium resonance is also observed growing in at δ 1.07 ppm indicating deuteration of the thiol (i.e., RSD).

To further examine the deuterium exchange from alkyne-d to thiol, phenylacetylene-d (2B-d), t-butylmercaptan, and Zr-i were dissolved in benzene-d₆ and heated at 120° C. for 9 hours. Despite no evidence of zirconium-mediated hydrothiolation, deuterium/proton exchange is observed by $^1$H and $^2$H NMR spectroscopy, indicating that the exchange is independent of the zirconium-mediated hydrothiolation pathway. A similar combination of 2B-d and 1A without catalyst evidences no deuterium exchange showing that zirconium is involved in the isotopic exchange process.

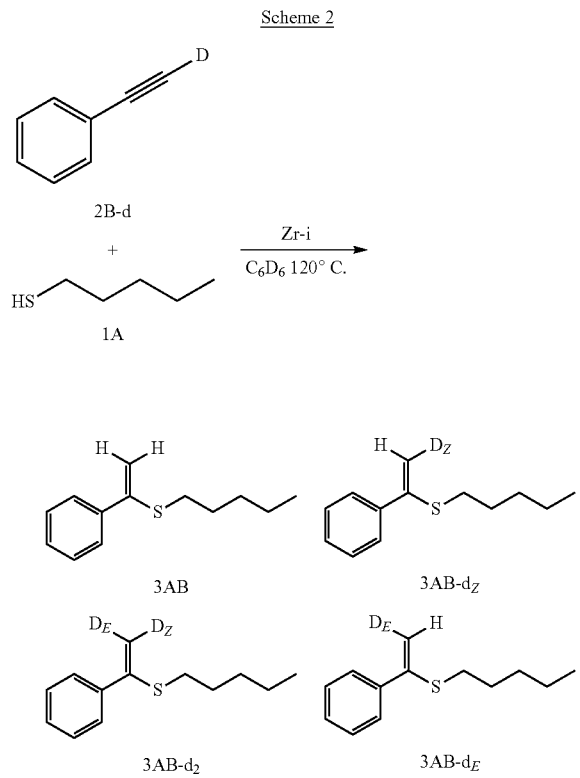

Figure 2A:
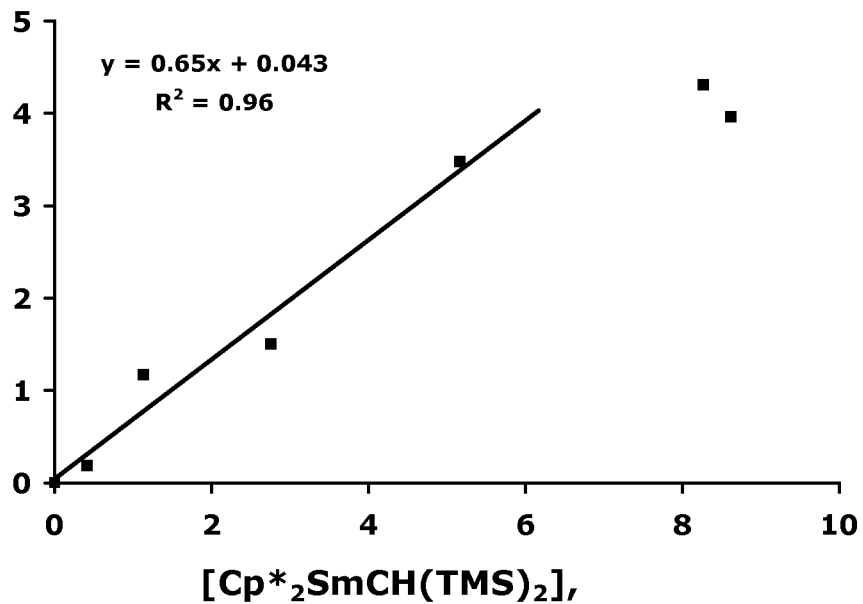
FIG. 2 is a plot of product formation rate for the reaction 1A+2B→3AB as a function of [Cp*$_2$SmCH(TMS)$_2$ (Ln-ix)] (A) and [2B](B) with [1A] and [2B]=0.2 M; (C) plot of hydrothiolation conversion (%) versus time with 17× molar excess 2A over 1A exhibits a linear trend indicating a pseudo-zero-order reaction, demonstrating rate independence with respect to [1A] except at the highest concentrations where catalyst precipitation becomes extensive.
Figure 2B:
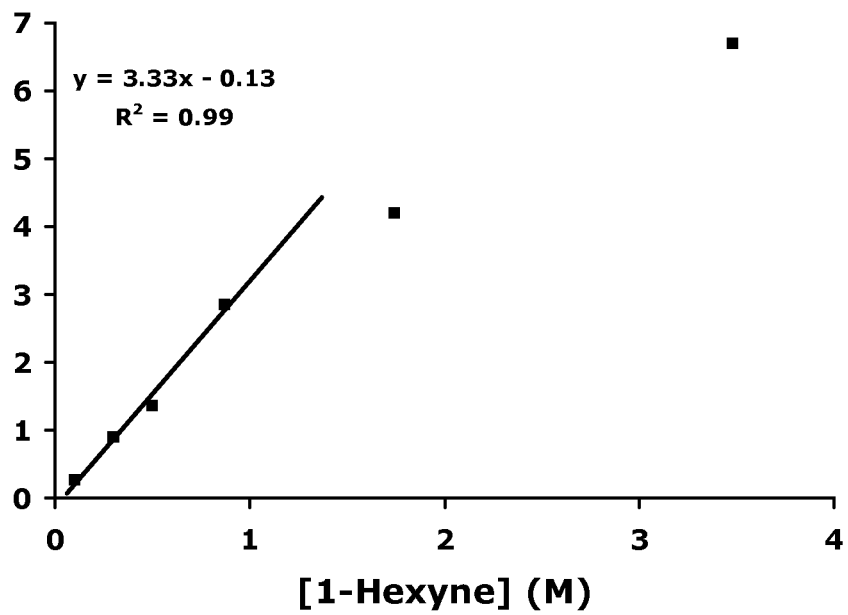
Figure 2C:
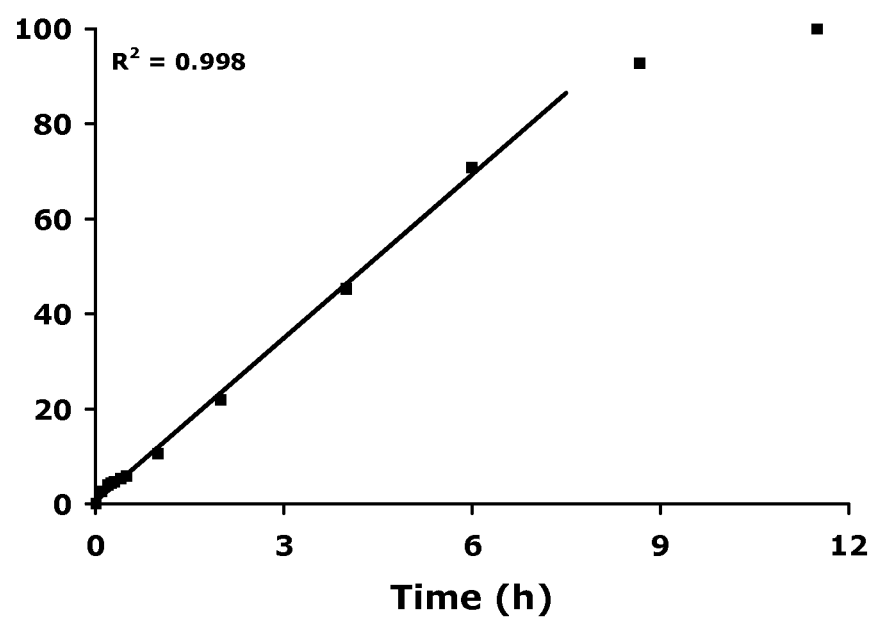

Kinetic experiments are also conducted on the Ln-ix-mediated hydrothiolation of 2A by 1A in benzene-$d_6$ at 120° C. The empirical rate law is derived by examining the turnover-frequency ($N_t$) while systematically varying [catalyst], [alkyne], and [thiol]. By examining Ln-ix from 0.4-8.6 mM, a linear trend is observed for concentrations of 0.4-5.2 mM (FIG. 2A), indicating a first-order dependence on [catalyst] at lower concentrations, while a fall in activity is observed at higher concentrations. Attempts to explore the reaction at even higher Ln-ix values, 9-17 mM, results in reduced activity and rapid catalyst precipitation from solution. An investigation of the effects of increasing [1-hexyne] from 0.1-3.5 M reveals a linear correlation with activity over the [1-hexyne] range, 0.1-0.9 M (FIG. 2B), indicating initial first-order dependence on [alkyne]. On increasing the alkyne concentration further, a slight reduction in activity is observed which may be the result of partial alkyne saturation of the metal center and/or alkyne acting as a hydrothiolation inhibitor. Finally, the dependence of $N_t$ on [1-penthanethiol] from 0.01-0.2 M at 1-hexyne concentrations (i.e., 3.5 M) to force the reaction to pseudo zero-order shows the reaction to be zero-order with respect to [thiol] (FIG. 2C). The fall in rate near the end of the reaction corresponds to the onset of observable catalyst precipitation. Therefore, the empirical rate law, under standard catalytic conditions with minimal catalyst precipitation, is given by Equation 1b.

$$\text{Rate} = k_{obs}[\text{Sm}]^1[\text{Alkyne}]^1[\text{Thiol}]^0 \qquad \text{(Equation 1b)}$$

To trace the fate of D-C≡C—R' during Ln-ix- and An-i-mediated hydrothiolation, deuterium-labeling studies are performed using deuterated 2B-d and 1A. Exclusive observation of $H_2C(TMS)_2$ in the $^1$H and $^2$H NMR evidences thiol-mediated protonolytic activation of the catalyst. By comparing the activity with that of non-deuterated phenylacetylene, apparent KIEs of $k_H/k_D$=1.40(0.1) and 1.35(0.1) are observed for catalysts Ln-ix and An-i, respectively. This is consistent with a secondary kinetic isotope effect in a turnover-limiting insertion mechanism. At early reaction times, a single product isotopomer is primarily observed. However, upon further heating, other known isotopomer products are observed, along with substantial loss of the phenylacetylene deuterium label. The observation of 3AB-dE product early in the reaction is consistent with thiol-mediated protonolysis. As the reaction progresses, increasing quantities of other product isotopomers form, corresponding to redistribution of the alkyne $^2$H label. Based on $^1$H and $^2$H NMR spectroscopy, deuterium is observed to migrate from the alkyne terminus to the thiol functionality, as evidenced by a prominent RSD resonance in the 2H NMR. To determine if the migration is the result of the catalytic cycle, t-butylmercaptan, phenylacetylene-d, and either complex Ln-ix or An-i are heated in benzene-$d_6$ at 120° C. for 0.75 hours. Proton NMR integration indicates that 15-30% of the deuterium migrates from the alkyne during this time period despite the fact that no measurable hydrothiolation product is observed. A control experiment without the addition of catalyst results in no detectable deuterium scrambling. The observed $^2$H exchange between phenylacetylene-d and t-BuSH, prior to significant catalytic turnover, as well as negligible $^2$H migration in the absence of catalyst, strongly supports a metal complex pathway independent of the hydrothiolation catalytic cycle. The known protonolytic reactivity of terminal alkynes, with lanthanide- and actinide-heteroelement bonds suggests a pathway such as shown in Scheme 3.

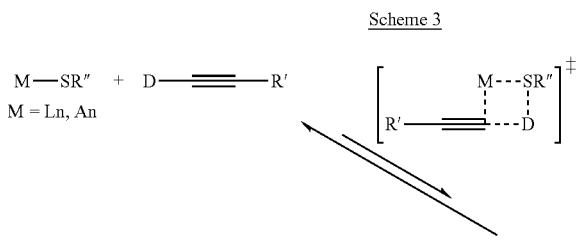

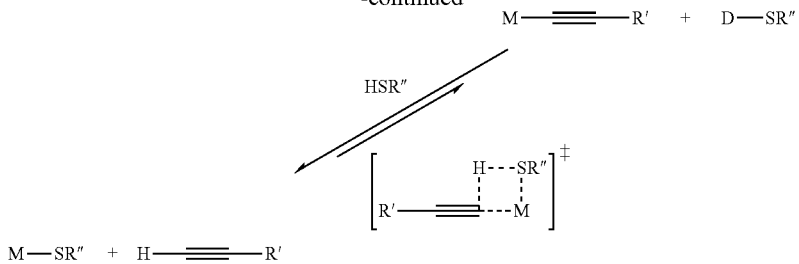

Interestingly, the more rapid formation of the product isotopomers in lanthanide- and actinide-mediated hydrothiolation than in zirconium-mediated hydrothiolation is consistent with the more polar bonding and larger ionic radii of lanthanide and actinide complexes and lanthanide and actinide complexes exhibiting a lower protonolytic/deuterolytic barrier. Bond enthalpy estimates indicate that the protonolytic detachment of alkyne from organo-Th or Sm complexes is ca. −24 kcal/mol and −22 kcal/mol, respectively (Equation 2).

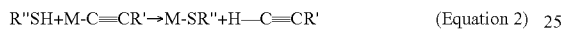

R″SH+M-C≡CR′→M-SR″+H—C≡CR′ (Equation 2)

Due to the Markonikov selectivity and exothermicity of thiol-mediated protonolysis of metal-alkynyl bonds, the metal-alkynyl ↔ metal-thiolate equilibrium should strongly favor the corresponding thiolates. In the Ln-ix- and An-i-mediated hydrothiolation of phenylacetylene-d by 1A, the formation of primarily 3AB-$d_2$ further supports the insertion/thiol-mediated protonolysis mechanism (Scheme 4). The observation of small quantities of 3AB early in the reaction demonstrates the rapid nature of deuterium/proton scrambling between the alkyne and thiol positions.

Scheme 4

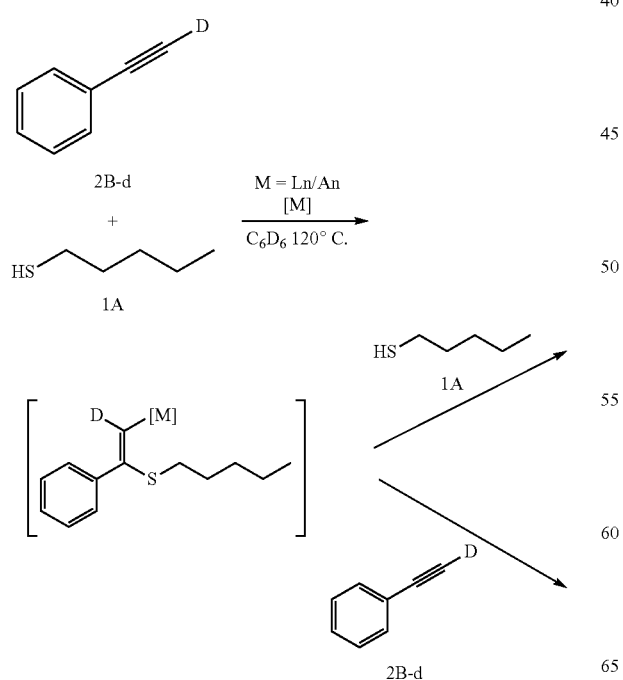

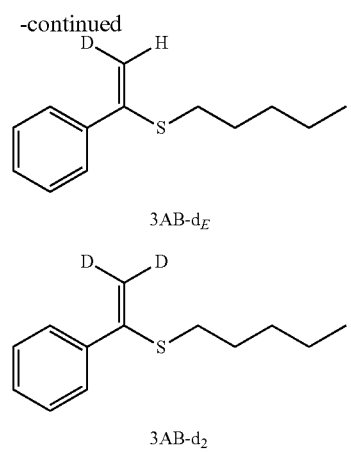

While alkyne deuterolysis of M-vinyl product from the lanthanide or actinide center could result in $^2$H delivery to the Z product position, it seems more likely to originate from thiol-mediated deuterolysis of products bound to the metal center (Scheme 5), because of the RSD detected in situ by $^2$H NMR, and REH (E=O and S) protonolysis pathways in analogous organozirconium-mediated hydrothiolation and lanthanide-mediated hydroalkoyxlation processes.

Scheme 5

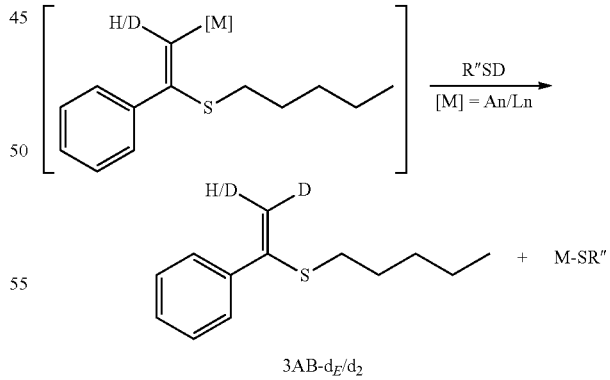

The disclosures in this application of all articles and references, including patents, are incorporated herein by reference.

The invention is illustrated further by the following examples which are not to be construed as limiting the invention in scope or spirit to the specific procedures described herein. The starting materials and various intermediates may be obtained from commercial sources, prepared from commercially available compounds, or prepared using well known synthetic methods. Representative examples of methods for preparing intermediates of the invention are set forth below. All thiols, alkynes and vinyl sulfide products of the examples below are named by ChemBioDraw Ultra, version 12.0.

EXAMPLES

Materials and Methods

Due to the air and moisture sensitivity of the organoactinide complexes in this study, all manipulations are carried out in oven-dried, Schlenk-type glassware interfaced to either a dual-manifold Schlenk line, high-vacuum line ($10^{-6}$ Torr), or in a nitrogen-filled glove box (<2 ppm $O_2$). Argon (Airgas) is further purified by passing it through columns of MnO and activated 4 A Davison molecular sieves immediately before use. Toluene-$d_8$ and benzene-$d_6$ (all 99+ atom % D) for NMR reactions and kinetic measurements are stored over Na/K alloy in vacuo and vacuum transferred immediately prior to use or are stored in a nitrogen-filled glovebox until use. Diethylether for synthesis is distilled from Na/benzophenone immediately prior to use. $D_2O$ (99+ atom % D) is used as received. Tetraglyme is vacuumed-pumped to remove volatiles. Ethanethiol-d (98 atom % D) is prepared according to literature methods (Marks et al., *J. Am. Chem. Soc.* 2009, 131, 2062-2063). Thiols and alkynes are transferred from multiple beds of activated Davison 4 A molecular sieves as solutions in benzene-$d_6$ or neat, followed by degassing ($10^{-6}$ Torr) via freeze-pump-thaw methods. Conjugated alkynes and thiols are stored at $-10°$ C. until use. All substrates are stored under argon until use, and phenylacetylene and 1-ethynylcyclohexene are distilled just prior to use. The catalysts are prepared as reported in the literature (see Stubbert; B. D., Marks, T. J. *J. Am. Chem. Soc.* 2007, 129, 6149-6167; Stubbert, B. D.; Marks, T. J. *J. Am. Chem. Soc.* 2007, 129, 4253-4271; and Stubbert, B. D.; Stern, C. L.; Marks, T. J. *Organometallics* 2003, 22, 4836-4838, all of which are incorporated herein by reference). The methyltriphenylsilane $^1$H NMR internal integration standard for kinetics is sublimed under high-vacuum and stored in a glove box until use.

Physical and Analytical Measurements.

NMR spectra are recorded on Mercury 400 (400 MHz, $^1$H; 100 MHz, $^{13}$C; 61 MHz, $^2$H) and Avance III 500 (500 MHz, $^1$H; 125 MHz, $^{13}$C) NMR spectrometers. Chemical shifts (δ) are referenced relative to internal solvent or integration standard resonances and reported relative to $Me_4Si$. Spectra of air-sensitive reactions and materials are taken in airtight, Teflon-valved J. Young NMR tubes. Samples are heated in silicon oil baths with the temperature controlled by an Ika ETS-D4 probe. GC data for selectivity measurements are collected on a HP6890 GC-MS equipped with a HP5972 detector and an HP-5MS (5% phenyl methyl siloxane, 30 m×250 μm×0.25 μm) capillary column while high-resolution mass spectra are collected on an Agilent 6210 LC-TOP (ESI, APPI) and Thermo Finnegan MAT900 (EI).

Typical NMR Scale Catalytic Reaction.

a) In a glove box, Zr-i (3.7 mg, 10 μmol) and methyltriphenylsilane (8.0 mg, 29.5 μmol) are dissolved in 0.6 ml of $C_6D_6$ and added to a J. Young NMR tube. The tube is sealed, removed from the glove box, and attached to a high-vacuum line where 0.2 ml of thiol and 0.2 ml of alkyne solutions (both 1.0 M in benzene-$d_6$; 0.2 mmol; 20-molar excess) are syringed in under an argon flush. The reaction mixture is then sealed, shaken well, degassed by a single freeze-pump-thaw cycle, and placed in a pre-heated, temperature controlled oil bath covered with aluminum foil.

b) In a glove box, Ln-ix (3.0 mg, 5.2 μmol) and methyltriphenylsilane (8.0 mg, 29.5 μmol) are dissolved in 0.6 ml benzene-$d_6$ and added to a J. Young NMR tube. The tube is sealed, removed from the glove box, and attached to a high-vacuum line where 0.2 ml of thiol and 0.2 ml of alkyne solutions (both 1.0 M in benzene-$d_6$; 0.2 mmol; 38-molar excess) are syringed in under an argon flush. The reaction mixture is then sealed, shaken well, degassed by a single freeze-pump-thaw cycle, and placed in a pre-heated, temperature controlled oil bath covered with aluminum foil.

Typical NMR Scale Kinetic Experiment. The same procedure as described above is followed except that the sample is periodically cooled to room temperature to collect $^1$H NMR spectra. Turnover frequency ($N_t$) is determined by the method of initial rate where data points are collected early in the reaction before the substrates are appreciably consumed. As a result, the reaction during this period of time is approximated as pseudo-zero-order with respect to the substrate concentrations, resulting in a linear trend. The resulting linear plots are fit by a linear-regression analysis using $R^2 \geq 0.99$ according to Equation 3, and $N_t$ is calculated according to Equation 4 where $[catalyst]_0$=initial concentration of catalyst and t=time in hours. Kinetic experiments in this study are performed at 0.2 M [thiol] and [alkyne] unless otherwise indicated. Linear corrections for slight variations in initial [thiol] and [alkyne] are applied as needed.

$$[\text{product}] = mt \qquad \text{Equation 3}$$

$$N_t(h^{-1}) = \frac{m}{[catalyst]_0} \qquad \text{Equation 4}$$

Yield and Selectivity Measurements.

a) In the glovebox, Zr-iv (5.0 mg, 10 μmol) is dissolved in 0.4 ml of $C_6D_6$ and the resulting solution is transferred to a J. Young NMR tube. The tube is then sealed, removed from the glovebox, and attached to a high-vacuum line where 0.2 ml of thiol and 0.6 ml of alkyne solutions (both 1.0 M in benzene-$d_6$; 0.2 mmol; 20-molar excess in thiol) are syringed in under an argon flush. The reaction mixture is then sealed, shaken, degassed by a single freeze-pump-thaw cycle, and placed in a temperature-controlled, $120°$ C. oil bath for 24.0 hours. The product conversion and selectivity are determined by $^1$H NMR and GC/MS.

b) In a glove box, Ln-ix (5.0 mg, 10 μmol) is dissolved in 0.4 ml benzene-$d_6$ and the resulting solution transferred to a J. Young NMR tube. The tube is then sealed and attached to a high-vacuum line where 0.2 ml thiol and 0.6 mL alkyne solutions (both 1.0 M in benzene-d6; 0.2 mmol; 20-molar excess in thiol) are syringed in under an argon flush. The reaction mixture is then sealed, shaken, and placed in temperature-controlled, $120°$ C. oil bath for 16.0 hours. The product selectivity is determined by GC/MS while conversion is determined by $^1$H NMR integrations against internal standards or quantitatively liberated catalyst ligands.

General Procedure for Purification of Products.

The reaction mixture is cooled to room temperature and the contents are eluted through a silica gel plug with ~10 ml of hexanes to remove the catalyst. The filtrate is pumped with a Schlenk line to remove volatiles. Further purification by flash chromatography (ether:hexanes eluent) is performed when necessary. To avoid degradation, some products are purified by precipitating the catalyst from exposure to air, centrifuging the precipitated catalyst, and decanting the solution. Volatiles are pumped off on a Schlenk line to yield pure product.

General Preparative Scale Procedure.

a) In a glovebox, Zr-iv (220 mg, 0.44 mmol) is added to an oven-dried, 20 ml J. Young-valved glass storage tube with a stir bar and dissolved in 10 ml of toluene. The tube is then sealed and placed on a high-vacuum line where 1A (1.0 ml, 8.1 mmol) and 2A (2.5 ml, 22 mmol) are syringed into the tube under an argon flush. The vessel is next sealed and placed in a preheated 100° C. oil bath for 24 hours. After cooling, the vessel is opened to ambient and the catalyst is removed by filtering through silica gel, eluting with ~20 ml of hexanes. The volatiles are then removed under vacuum to yield pure 3AA as a yellow oil (1.08 g, 5.8 mmol, 72% yield) which is determined to be 99% Markovnikov pure by GC/MS.

b) In a glove box, Ln-ix (75 mg, 0.13 mmol) is added to an oven dried, 20 ml Teflon-valved, glass storage tube dissolved in 1 ml benzene. On a high-vacuum line, an additional 9 ml of benzene are added by vacuum transfer. The tube is cooled to −78° C. and 2A (7, 0.90 ml, 7.8 mmol) and 1F (0.30 ml, 2.6 mmol) are syringed into the tube under an argon flush. The vessel is sealed, thawed, and placed in a pre-heated 120° C. oil bath for 36.0 hours with no stirring. Under ambient conditions, the catalyst is removed by filtering through silica gel and eluting with 20 ml hexanes. The volatiles are then removed under vacuum ($10^{-6}$ mTorr) to yield 97% Markovnikov-pure 3FA as a yellow oil (0.22 g, 1.1 mmol, 41% yield).

Example 1 a) pentane-1-thiol-d

(1A-d)

An oven-dried, 200 ml Schlenk flask is charged with LiH (0.72 g, 91 mmol) and a magnetic stir bar. While under nitrogen, 50 ml of dry tetraglyme is cannulated into the flask and stirred vigorously to form a slurry. The flask is cooled to 0° C. before dropwise addition of dry 1A (8.4 g, 80.6 mmol). The reaction is allowed to warm to room temperature and then stirred for 1 hour followed by recooling to 0° C. and dropwise quenching with $D_2O$ (2.5 ml, 140 mmol). The product 1A-d is vacuum-transferred from the tetraglyme and dried over 4 A molecular sieves before use (~2.5 g, 30% yield). $^1$H NMR (benzene-$d_6$, 400 MHz, δ): δ 2.17 (q, J=7.2 Hz, 2H); 1.34 (m, 2H); 1.12 (m, 4H); 0.79 (t, J=5.6 Hz, 3H). $^2$H NMR (benzene-$d_6$, 76.7 MHz, δ): δ 1.09 (s). $^{13}$C NMR (benzene-$d_6$, 100 MHz, δ): δ 33.9; 30.8; 24.9; 22.3; 14.2.

Ethanethiol-d (1E-d)-$^1$H NMR (benzene-$d_6$, 500 MHz, δ): δ 2.16 (m, 2H); 0.97 (t, 7.0 Hz, 1H). $^{13}$C NMR (benzene-$d_6$, 125 MHz, δ): δ 20.1; 19.3. 2H (benzene-$d_6$, 61 MHz, δ): δ 1.07 (s).

Example 2 a) phenylacetylene-d

In an oven-dried, 200 ml Schlenk flask, phenylacetylene (7.0 ml, 64 mmol) is dissolved in 60 ml of anhydrous diethylether. The flask is cooled to 0° C. before the slow addition of 45 ml of n-BuLi solution (1.6 M in hexanes, 72 mmol) and stirring for 15 minutes at 0° C., followed by 30 minutes at room temperature. The flask is recooled to 0° C., and $D_2O$ (2.5 ml, 125 mmol) is slowly added. The reaction is stirred overnight at room temperature before the solvent is removed in vacuo, and the product is distilled to afford a clear liquid in 57% yield. The deuterium incorporation is determined to be 98% atom % D by $^1$H NMR. $^1$H NMR (benzene-$d_6$, 500 MHz, δ): δ 7.40 (m, 2H); 6.91 (m, 3H). $^{13}$C NMR (benzene-$d_6$, 125 MHz, δ): δ 132.7; 129.1; 128.9; 123.1; 83.8 (t, 7.5 Hz); 78.0 (t, 38 Hz). 2H (benzene-$d_6$, 61 MHz, δ): δ 2.68 (s).

Example 3 a) hex-1-en-2-yl(pentyl)sulfane

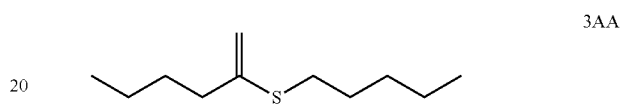

3AA

In a glove box, An-iv (140 mg, 0.25 mmol) is added to an oven-dried, J. Young-valved glass tube with stir bar. The tube is sealed, placed on a high-vacuum line where toluene (30 ml) is vacuum transferred from Na/K to dissolve the catalyst. Under an argon flush, 1A (0.60 ml, 4.8 mmol) and 2A (0.65 m, 5.7 mmol) are syringed into the tube, degassed by freeze-pump-thaw, sealed, and placed in a pre-heated 120° C. oil bath for 24 hours. Next, the vessel is opened to ambient surroundings and catalyst is removed by filtering through silica gel and eluting with hexanes. The product is purified by flash chromatography ($SiO_2$, eluted with 5:1 hexanes/ethyl acetate) and pumped down on a Schlenk line to yield pure 3AA as a yellow oil (0.62 g, 3.3 mmol, 69% yield).

$^1$H NMR (benzene-$d_6$, 400 MHz, δ): δ 5.34 (s, 1H); 4.72 (s, 1H); 2.53 (t, J=7.2 Hz, 2H); 2.25 (t, J=8.0 Hz, 2H); 1.63-1.47 (m, 4H); 1.34-1.08 (m, 6H); 0.90-0.75 (m, 6H). $^{13}$C NMR (benzene-$d_6$, 125 MHz, δ: δ 147.2; 105.1; 38.2; 31.9; 31.8; 31.7; 28.6; 22.9; 22.8; 14.5; 14.4. HRMS-EI (m/z): M$^+$ calcd for $C_{11}H_{22}S$, 186.144. found, 186.144. 95% yield; 94% Markovnikov-selective.

Example 4

The following compounds are prepared using essentially the same procedure as that described in the schemes, with reaction temperature as that found in Table 2, and the general and specific examples of above.

a) cyclohexyl(hex-1-en-2-yl)sulfane

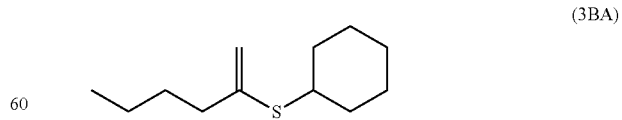

(3BA)

(yellow oil) $^1$H NMR (benzene-$d_6$, 500 MHz, δ): δ 5.07 (s, 1H); 4.85 (s, 1H); 2.94 (m, 1H); 2.22 (t, J=7.5 Hz, 2H); 1.98 (m, 2H); 1.57 (m, 4H); 1.38 (m, 3H); 1.27 (m, 2H); 1.11 (m, 3H); 0.85 (t, J=7.5 Hz, 3H). $^{13}$C NMR (benzene-$d_6$, 125 MHz, δ): δ 145.8; 107.4; 50.42; 43.4; 38.4; 33.5; 31.7; 26.5; 22.8;

14.4. HRMS-EI (m/z): M+ calcd for $C_{12}H_{22}S$ 198.144. found, 198.144. 55% yield; 59% Markovnikov-selective.

b) hex-1-en-2-yl(4-methylbenzyl)sulfane

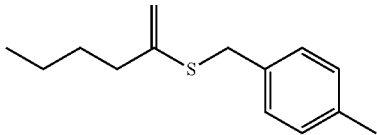

(3CA)

(dark yellow oil) $^1$H NMR (benzene-$d_6$, 400 MHz, δ): δ 7.20-7.14 (m, 2H); 6.94-6.90 (m, 2H); 5.00 (s, 1H); 4.76 (s, 1H); 3.72 (s, 2H); 2.21 (m, 3H); 2.06 (s, 3H); 1.53 (m, 2H); 1.22 (m, 2H); 0.81 (m, 3H). $^{13}$C NMR (benzene-$d_6$, 100 MHz, δ): δ 147.2; 137.1; 134.5; 129.8; 129.5; 106.2; 38.0; 36.6; 31.7; 22.7; 21.3; 14.4. HRMS-EI (m/z): M+ calcd for $C_{14}H_{20}S$, 220.129. found, 220.128.

c) pentyl(1-phenylvinyl)sulfane

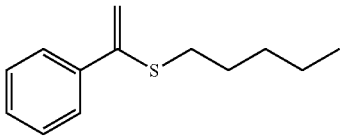

(3AB)

(dark yellow oil) $^1$H NMR (benzene-$d_6$, 500 MHz, δ): δ 7.63 (d, J=7.5 Hz, 2H); 7.12 (dd, J=7.5 Hz, 2H); 7.07 (m, 1H); 5.41 (s, 1H); 5.14 (s, 1H); 2.48 (t, J=7.5 Hz, 2H); 1.48 (t, J=7.5 Hz, 2H); 1.20-1.05 (m, 4H); 0.77 (t, J=7.0 Hz, 3H). $^{13}$C NMR (benzene-$d_6$, 125 MHz, δ): δ 140.5; 129.0; 128.9; 127.9; 110.7; 32.6; 28.9; 22.9; 21.6; 14.4. HRMS-EI (m/z): M+ calcd for $C_{13}H_{18}S$, 206.113. found, 206.113. 100% yield; 66% Markovnikov-selective.

d) (1-(cyclohex-1-en-1-yl)vinyl)(pentyl)sulfane

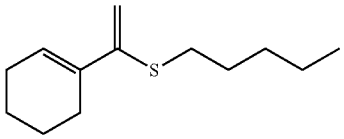

(3AC)

(dark yellow oil) $^1$H NMR (benzene-$d_6$, 500 MHz, δ): δ 6.43 (s, 1H); 5.29 (s, 1H); 4.97 (s, 1H); 2.54 (t, J=7.5, 2H); 2.23-2.18 (m, 2H); 1.99-1.94 (m, 2H); 1.58-1.50 (m, 2H); 1.52-1.47 (m, 2H); 1.42-1.36 (m, 2H); 1.27-1.19 (m, 2H); 1.20-1.12 (m, 2H); 0.80 (t, J=7.0, 3H). $^{13}$C NMR (benzene-$d_6$, 125 MHz, δ): δ 147.1; 136.4; 1277; 107.2; 32.5; 31.8; 29.0; 27.7; 26.3; 23.5; 23.0; 22.8; 14.5. HRMS-EI (m/z): M+ calcd for $C_{13}H_{22}S$, 210.144. found 210.143. 100% yield; 75% Markovnikov-selective.

e) (1-cyclohexylvinyl)(pentyl)sulfane

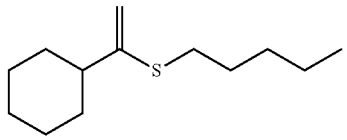

(3AD)

(yellow oil) $^1$H NMR (benzene-$d_6$, 500 MHz, δ): δ 5.07 (s, 1H); 4.67 (s, 1H); 2.53 (t, J=7.0 Hz, 2H); 2.14 (t, J=11.5 Hz, 1H); 1.98 (d, J=12.5 Hz, 2H); 1.68 (d, J=12.5 Hz, 2H); 1.54 (t, 7.5, 3H); 1.40 (m, 2H); 1.25-1.02 (m, 7H); 0.80 (t, J=7.0 Hz, 3H). $^{13}$C NMR (benzene-$d_6$, 125 MHz, δ): δ 153.1; 102.7; 47.1; 33.9; 31.9; 31.6; 28.5; 27.3; 26.8; 23.0; 14.5. HRMS-EI (m/z): M+ calcd for $C_{13}H_{24}S$, 212.160. found, 212.159. 92% yield; 92% Markovnikov-selective.

f) (1-cyclohexylvinyl)(4-methylbenzyl)sulfane

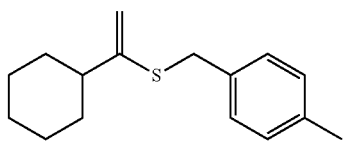

(3CD)

(dark yellow oil) $^1$H NMR (benzene-$d_6$, 400 MHz, δ): δ 7.16 (d, J=8.0 Hz, 2H); 6.92 (d, J=8.0 Hz, 2H); 5.05 (s, 1H); 4.71 (s, 1H); 3.73 (s, 2H); 2.11 (m, 1H); 2.07 (s, 3H); 1.96 (m, 2H); 1.64 (m, 2H); 1.52 (m, 2H); 1.37 (m, 2H); 1.11 (m, 3H). $^{13}$C NMR (benzene-$d_6$, 100 MHz, δ): δ 153.0; 137.0; 134.5; 129.7; 129.5; 103.8; 46.9; 36.6; 33.8; 27.2; 26.8; 21.4. HRMS-EI (m/z): M+ calcd for $C_{16}H_{22}S$, 246.144. found, 246.144.

g) ethyl(hex-1-en-2-yl)sulfane

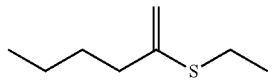

3EA $^1$H NMR (benzene-$d_6$, 500 MHz, δ): δ 5.01 (s, 1H); 4.66 (s, 1H); 2.43 (q, 7.5 Hz, 2H); 2.22 (t, 7.5 Hz, 2H); 1.55 (m, 2H); 1.24 (m, 2H); 1.06 (t, 7.5 Hz, 3H); 0.83 (t, 7.5 Hz, 3H). $^{13}$C NMR (benzne-$d_6$, 125 MHz, δ): δ 146.8; 105.2; 38.1; 31.8; 25.6; 22.7; 14.4; 13.7. HRMS (EI) m/z calcd for $C_8H_{16}S$: 144.0973. found: 144.0966. 95% yield; 96% Markovnikov-selective.

h) hex-1-en-2-yl(2,2,2-trifluoroethyl)sulfane

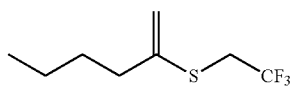

3FA

¹H NMR (benzene-d₆, 400 MHz, δ): δ 4.90 (s, 1H); 4.75 (s, 1H); 2.69 (q, 10 Hz, 2H); 2.00 (t, 7.6 Hz, 2H); 1.34 (m, 2H); 1.40-1.30 (m, 2H); 1.17-1.07 (m, 2H); 0.78 (t, 7.2 Hz, 3H). ¹³C NMR (benzene-d₆, 100 MHz, δ): δ 143.5; 129.0; 110.2; 36.9; 33.8 (q, $J_{FC}$=10 Hz); 31.0; 22.5; 14.3. HRMS (EI) m/z calcd for $C_8H_{13}F_3S$: 198.0690. found: 198.0684. 79% yield; 84% Markovnikov-selective.

i) benzyl(hex-1-en-2-yl)sulfane

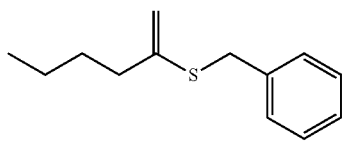

3GA

¹H NMR (benzene-d₆, 500 MHz, δ): δ 7.22 (d, 7.5 Hz, 2H); 7.08 (t, 8.0 Hz, 2H); 7.01 (t, 7.5, 1H); 4.98 (s, 1H); 4.73 (s, 1H), 3.69 (s, 2H); 2.19 (t, 7.5 Hz, 2H); 1.51 (m, 2H); 1.22 (m, 2H); 0.81 (t, 7.5, 3H). ¹³C NMR (benzene-d₆, 125 MHz, δ): δ 147.0; 137.6; 129.5; 129.0; 127.6; 106.3; 37.9; 36.8; 31.7; 22.7; 14.4. HRMS (EI) m/z calcd for $C_{13}H_{18}S$: 206.1129. found: 206.1127. 95% yield; 95% Markovnikov-selective.

j) (3-cyclohexylprop-1-en-2-yl)(pentyl)sulfane

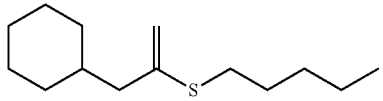

3AE

¹H NMR (benzene-d₆, 500 MHz, δ): δ 5.02 (s, 1H); 4.74 (s, 1H); 2.53 (t, 7.0 Hz, 2H); 2.18 (d, 7.0 Hz, 2H); 1.83-1.78 (m, 2H); 1.78-1.70 (m, 1H); 1.70-1.63 (m, 2H); 1.63-1.56 (m, 1H); 1.56-1.48 (m, 2H); 1.26-1.04 (m, 7H); 0.87-0.78 (m, 5H). ¹³C NMR (benzene-d₆, 125 MHz, δ): δ 145.5; 106.0; 46.7; 37.3; 33.6; 31.9; 31.7; 28.6; 27.3; 27.0; 22.9; 14.5. HRMS (EI) m/z calcd for $C_{14}H_{26}S$: 226.1755. found: 226.1748. 98% yield; 96% Markovnikov-selective.

k) pentyl(3-phenylprop-1-en-2-yl)sulfane

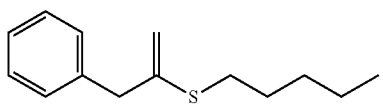

3AF

¹H NMR (benzene-d₆, 500 MHz, δ): δ 7.20-7.16 (m, 2H); 7.15-7.10 (m, 2H); 7.06-7.01 (m, 1H); 4.96 (s, 1H); 4.73 (s, 1H); 3.44 (s, 2H); 2.42 (t, 7.5 Hz, 2H); 1.44-1.36 (m, 2H); 1.13-1.01 (m, 4H); 0.72 (t, 7.0 Hz, 3H). ¹³C NMR (benzene-d₆, 125 MHz, δ): δ 146.4; 139.5; 129.7; 128.9; 127.1; 107.1; 44.5; 31.9; 31.8; 28.5; 22.9; 14.4. HRMS (EI) m/z calcd for $C_{14}H_{20}S$: 220.1286. found: 220.1287. 100% yield; 91% Markovnikov-selective.

l) 3-(1-(pentylthio)vinyl)pyridine

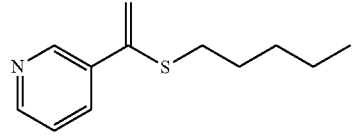

3AG

¹H NMR (benzene-d₆, 500 MHz, δ): δ 9.05 (s, 1H); 8.46 (dd, 5.0 Hz, 1H); 7.59 (dt, 8.0 Hz, 1H); 6.66 (dd, 8.0 Hz, 1H); 5.24 (s, 1H); 5.04 (s, 1H); 2.37 (t, 7.5 Hz, 2H); 1.40 (m, 2H); 1.15-1.05 (m, 4H); 0.77 (t, 7.0 Hz, 3H). ¹³C NMR (benzene-d₆, 125 MHz, δ): δ 150.4; 149.2; 143.2; 136.1; 134.5; 123.4; 112.0; 32.5; 31.5; 28.7; 22.8; 14.4. HRMS (APPI) m/z [M+H]⁺ calcd for $C_{12}H_{17}NS$: 208.1161. found: 208.1158. 100% yield; 90% Markovnikov-selective.

m) 2-(pentylthio)prop-2-en-1-amine

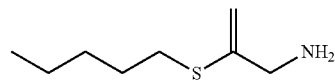

3AH

¹H NMR (benzene-d₆, 500 MHz, δ): δ 5.16 (s, 1H); 4.74 (s, 1H); 3.26 (s, 2H); 2.49 (t, 7.5 Hz, 2H); 1.49 (m, 2H); 1.26-1.06 (m, 4H); 0.87-0.63 (bm, 5H). ¹³C NMR (benzene-d₆, 125 MHz, δ): δ 149.5; 105.1; 48.8; 31.8; 31.5; 28.8; 22.9; 14.5. HRMS (ESI) m/z [M+H]⁺ calcd for $C_8H_{18}NS$: 160.1154. found: 160.1155.

Table 4 shows representative examples of compounds made and the catalyst and solvent employed. The reactions are performed at temperatures ranging from 90-120° C. While titanium is not specifically listed in the table, the metal is employed in complexes for methods of the invention. As with other Group 4 metals, optimization may vary with reaction conditions.

TABLE 4

| Thiol | Alkyne | Catalyst | Solvent |
|---|---|---|---|
| 1H (Dodecanethiol) | 2B | Ln-i | Benzene-d₆ |
| 1H | 2B | Ln-i | THF-d₈ |
| 1H | 2B | Ln-ii | Benzene-d₆ |
| 1H | 2A | Ln-i | Benzene-d₆ |
| 1C | 2B | Ln-i | Benzene-d₆ |
| 1A | 2A | Ln-v | THF-d₈ |
| 1B | 2A | Ln-i | Benzene-d₆ |
| 1B | 2A | Ln-ix | Benzene-d₆ |
| 1A | 2A | Ln-iv | THF-d₈ |
| 1D | 2A | Ln-v | THF-d₈ |
| 1D | 2A | Ln-ix | Benzene-d₆ |
| 1A | 2A | Ln-ii | Benzene-d₆ |
| 1A | 2A | Ln-vi | Benzene-d₆ |
| 1A | 2A | Ln-ix | Benzene-d₆ |
| 1G | 2A | Ln-ix | Benzene-d₆ |
| 1A | 2A | Zr-ii | Benzene-d₆ |
| 1A | 2A | An-iii | Benzene-d₆ |
| 1D | 2B | An-iv | Benzene-d₆ |

TABLE 4-continued

| Thiol | Alkyne | Catalyst | Solvent |
|---|---|---|---|
| 1D | 2B | An-ii | Benzene-$d_6$ |
| 1C | 2B | An-ii | Benzene-$d_6$ |
| 1A | 2B | An-iii | Benzene-$d_6$ |
| 1A | 2A | Zr-iii | Benzene-$d_6$ |
| 1A | 2A | Zr-ii | Benzene-$d_6$ |
| 1A | 2A | Zr-i | Benzene-$d_6$ |
| 1G | 2A | Zr-i | Benzene-$d_6$ |
| 1G | 2A | Zr-iii | Benzene-$d_6$ |
| 1G | 2A | Zr-iv | Benzene-$d_6$ |
| 1G | 2A | Zr-v | Benzene-$d_6$ |
| 1D | 2A | Zr-iii | Benzene-$d_6$ |
| 1A | 2D | Zr-i | Benzene-$d_6$ |
| 1A | 2D | An-vii | Benzene-$d_6$ |
| 1G | 2A | An-vii | Benzene-$d_6$ |
| 1D | 2B | An-vii | Benzene-$d_6$ |
| 1A | 2C | Zr-i | Benzene-$d_6$ |
| 1A | 2B | Zr-i | Benzene-$d_6$ |
| 1A | 2G | Zr-i | Benzene-$d_6$ |
| 1A | 2E | Zr-i | Benzene-$d_6$ |
| 1A | 2H | Zr-iii | Benzene-$d_6$ |
| 1A | 2H | Zr-i | Benzene-$d_6$ |
| 1B | 2A | Zr-i | Benzene-$d_6$ |
| 1H | 2A | Zr-i | Benzene-$d_6$ |
| 1H | 2A | Zr-iii | Benzene-$d_6$ |
| 1A | 2A | Zr-iv | Benzene-$d_6$ |
| 1H | 2A | Zr-iv | Benzene-$d_6$ |
| 1E | 2A | Zr-i | Benzene-$d_6$ |
| 1E | 2A | Ln-ix | Benzene-$d_6$ |
| 1F | 2A | Zr-i | Benzene-$d_6$ |
| 1D | 2A | Zr-i | Benzene-$d_6$ |
| 1A | 2F | Zr-i | Benzene-$d_6$ |

The catalytic organolanthanide-, organoactinide- and organozirconium-mediated intermolecular hydrothiolathion of a wide range of terminal alkynes by aliphatic, benzylic and aromatic thiols is demonstrated by the methods disclosed herein. The resulting vinyl sulfides are produced with high Markovnikov selectivity. Based on kinetic experiments and deuterium labeling, the reaction is proposed to proceed through an alkyne insertion-thiol protonolysis sequence with turnover-limiting alkyne insertion.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims.

What is claimed is:

1. A method of preparing a vinyl sulfide comprising treating a terminal alkyne with an aliphatic, benzylic or aromatic thiol in the presence of a catalyst selected from the group consisting of an organolanthanide-, organoactinide- and organoGroup-4-complex.

2. A method according to claim 1 wherein the vinyl sulfide is prepared with >90% Markovnikov selectivity.

3. A method according to claim 2 wherein the vinyl sulfide is prepared with no or substantially no double-thiolated side product.

4. A method according to claim 3 wherein the vinyl sulfide is prepared through an alkyne insertion pathway followed by a thiol-mediated protonolysis.

5. A method according to claim 4 wherein the alkyne insertion pathway is turnover-limiting.

6. A method according to claim 1 wherein the catalyst is selected from the group consisting of:
   $CGCM^1R^1_2$, wherein $M^1$ is selected from an actinide metal and Zr(IV), and $R^1$ is selected from $NMe_2$, $NEt_2$ and Me;
   $CGCM^2R^2$, wherein $M^2$ is lanthanide metal and $R^2$ is $N(TMS)_2$;
   $Cp^*_2M^1R^3_2$, wherein $R^3$ is selected from $NMe_2$, $NEt_2$, Me and $CH_2TMS$;
   $Cp^*_2M^2R^4$, wherein $R^4$ is selected from $N(TMS)_2$ and $CH(TMS)_2$;
   $Me_2SiCp''_2M^3R^5_2$, wherein $M^3$ is an actinide metal, and $R^5$ is selected from $CH_2TMS$ and Bn;
   $M^2[R^4]_3$,
   $Cp^*M^4R^6$, wherein $M^4$ is a Group 4 metal and $R^6$ is selected from $Bn_3$ and $Cl_2NMe_2$; and
   $M^3(R^3)_4$.

7. A method according to claim 6 wherein the catalyst is selected from $Cp^*_2SmN(TMS)_2$, $Me_2SiCp''_2Th[CH_2(TMS)]_2$, $CGCZrMe_2$, $Cp^*_2YCH(TMS)_2$, $Cp^*_2YN(TMS)_2$, $Me_2SiCp''_2UBn_2$, $Cp^*_2ZrMe_2$, $CGCSmN(TMS)_2$, $CGCU(NMe_2)_2$, $Cp^*ZrBn_3$, $La[N(TMS)_2]_3$, $CGCTh(NMe_2)_2$, $Zr[NMe_2]_4$, $Nd[N(TMS)_2]_3$, $U(NEt_2)_4$, $Cp^*ZrCl_2NMe_2$, $Lu[CH(TMS)_2]_3$, $Cp^*_2U(NMe_2)_2$, $Y[N(TMS)_2]_3$, $Cp^*_2Th(CH_2TMS)_2$, $Cp^*_2LaCH(TMS)_2$, $Cp^*_2U(CH_2TMS)_2$, $Cp^*_2SmCH(TMS)_2$, and $Cp^*_2LuCH(TMS)_2$.

8. A method according to claim 1 wherein the terminal alkyne is of a formula:

$$\equiv\text{-R'}$$

wherein R' is selected from the group consisting of alkyl, aryl, heteroaryl, cycloalkyl, arylalkyl, heteroarylalkyl and cycloalkylalkyl.

9. A method according to claim 8 wherein R' is selected from the group consisting of $C_1$-$C_6$-alkyl, aryl, heteroaryl, $C_3$-$C_7$-cyloalkyl, aryl-$C_1$-$C_6$-alkyl, heteroaryl-$C_1$-$C_6$-alkyl and $C_3$-$C_7$-cyloalkyl-$C_1$-$C_6$-alkyl.

10. A method according to claim 9 wherein the terminal alkyne is selected from the group consisting of 1-hexyne, ethynylcyclohexane, prop-2-ynylcyclohexane, 1-ethynylcyclohex-1-ene, 3-ethynylpyridine, prop-2-yn-1-amine and ethynylbenzene.

11. A method according to claim 1 wherein the thiol is of a formula:

$$\text{R''—SH}$$

wherein R'' is selected from the group consisting of alkyl, aryl, heteroaryl, cycloalkyl, arylalkyl, heteroarylalkyl and cycloalkylalkyl.

12. A method according to claim 11 wherein the R'' is selected from the group consisting of $C_1$-$C_{12}$-alkyl, aryl, heteroaryl, $C_3$-$C_7$-cyloalkyl and aryl-$C_1$-$C_6$-alkyl.

13. A method according to claim 12 wherein the thiol is selected from the group consisting of 1-pentanethiol, 1-dodecanethiol, cyclohexanethiol, 2-methyl-2-butanethiol, benzyl mercaptan, 4-methylbenzyl mercaptan, prop-2-yn-1-amine or thiophenol.

14. A method of preparing a vinyl sulfide comprising treating a thiol of the formula I $$\text{R''—SH} \qquad\qquad \text{I}$$

with an alkyne of formula II $$\equiv\text{-R'} \qquad\qquad \text{II}$$

to afford a corresponding vinyl sulfide of formula III

III in the presence of a catalyst selected from the group consisting of;

$CGCM^1R^1_2$, wherein $M^1$ is selected from an actinide metal and Zr(IV), and $R^1$ is selected from $NMe_2$, $NEt_2$ and Me;

$CGCM^2R^2$, wherein $M^2$ is lanthanide metal and $R^2$ is $N(TMS)_2$;

$Cp*_2M^1R^3_2$, wherein $R^3$ is selected from $NMe_2$, $NEt_2$, Me and $CH_2TMS$;

$Cp*_2M^2R^4$, wherein $R^4$ is selected from $N(TMS)_2$ and $CH(TMS)_2$;

$Me_2SiCp''_2M^3R^5_2$, wherein $M^3$ is an actinide metal, and $R^5$ is selected from $CH_2TMS$ and Bn;

$M^2[R^4]_3$;

$Cp*M^4R^6$, wherein $M^4$ is a Group 4 metal and $R^6$ is selected from $Bn_3$ and $Cl_2NMe_2$; and $M^3(R^3)_4$, wherein R' and R" are independently selected from the group consisting of alkyl, aryl, heteroaryl, cycloalkyl, arylalkyl, heteroarylalkyl and cycloalkylalkyl.

15. A method according to claim 14 wherein

R' is selected from the group consisting of $C_1$-$C_6$-alkyl, aryl, heteroaryl, $C_3$-$C_7$-cyloalkyl, aryl-$C_1$-$C_6$-alkyl, heteroaryl-$C_1$-$C_6$-alkyl and $C_3$-$C_7$-cyloalkyl-$C_1$-$C_6$-alkyl; and R" is selected from the group consisting of $C_1$-$C_{12}$-alkyl, aryl, heteroaryl, $C_3$-$C_7$-cyloalkyl and aryl-$C_1$-$C_6$-alkyl.

16. A method according to claim 15 wherein the terminal alkyne is selected from the group consisting of 1-hexyne, ethynylcyclohexane, prop-2-ynylcyclohexane, 1-ethynylcyclohex-1-ene, 3-ethynylpyridine, prop-2-yn-1-amine and ethynylbenzene.

17. A method according to claim 15 wherein the thiol is selected from the group consisting of 1-pentanethiol, 1-dodecanethiol, cyclohexanethiol, 2-methyl-2-butanethiol, benzyl mercaptan, 4-methylbenzyl mercaptan, prop-2-yn-1-amine or thiophenol.

18. A method according to claim 14 wherein the vinyl sulfide is prepared with >90% Markovnikov selectivity.

19. A method according to claim 18 wherein the vinyl sulfide is prepared with no or substantially no double-thiolated side product.

20. A method according to claim 19 wherein the vinyl sulfide is prepared through an alkyne insertion pathway followed by a thiol-mediated protonolysis.

21. A method according to claim 20 wherein the alkyne insertion pathway is turnover-limiting.

22. A method according to claim 14 wherein the catalyst is selected from $Cp*_2SmN(TMS)_2$, $Me_2SiCp''_2Th[CH_2(TMS)]_2$, $CGCZrMe_2$, $Cp*_2YCH(TMS)_2$, $Cp*_2YN(TMS)_2$, $Me_2SiCp''_2UBn_2$, $Cp*_2ZrMe_2$, $CGCSmN(TMS)_2$, $CGCU(NMe_2)_2$, $Cp*ZrBn_3$, $La[N(TMS)_2]_3$, $CGCTh(NMe_2)_2$, $Zr[NMe_2]_4$, $Nd[N(TMS)_2]_3$, $U(NEt_2)_4$, $Cp*ZrCl_2NMe_2$, $Lu[CH(TMS)_2]_3$, $Cp*_2U(NMe_2)_2$, $Y[N(TMS)_2]_3$, $Cp*_2Th(CH_2TMS)_2$, $Cp*_2LaCH(TMS)_2$, $Cp*_2U(CH_2TMS)_2$, $Cp*_2SmCH(TMS)_2$, and $Cp*_2LuCH(TMS)_2$.

* * * * *